(12) United States Patent
Kiss et al.

(10) Patent No.: US 9,464,011 B2
(45) Date of Patent: Oct. 11, 2016

(54) PROCESS FOR MAKING ALKYLATED AROMATIC COMPOUND

(71) Applicant: ExxonMobil Chemical Patents Inc., Baytown, TX (US)

(72) Inventors: Gabor Kiss, Hampton, NJ (US); Thomas E. Green, Hamilton, NJ (US); Terry E. Helton, Montgomery, TX (US); William C. Horn, Long Valley, NJ (US); William A. Lamberti, Stewartsville, NJ (US); Tan-Jen Chen, Kingwood, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 14/770,657

(22) PCT Filed: Mar. 6, 2014

(86) PCT No.: PCT/US2014/021235
§ 371 (c)(1),
(2) Date: Aug. 26, 2015

(87) PCT Pub. No.: WO2014/158978
PCT Pub. Date: Oct. 2, 2014

(65) Prior Publication Data
US 2016/0009613 A1    Jan. 14, 2016

Related U.S. Application Data

(60) Provisional application No. 61/804,957, filed on Mar. 25, 2013.

(30) Foreign Application Priority Data

Jun. 17, 2013  (EP) .................................. 13172273

(51) Int. Cl.
| | |
|---|---|
| *C07C 45/53* | (2006.01) |
| *C07C 37/08* | (2006.01) |
| *C07C 2/66* | (2006.01) |
| *B01J 37/00* | (2006.01) |
| *B01J 35/00* | (2006.01) |
| *C07C 2/74* | (2006.01) |
| *C07C 407/00* | (2006.01) |
| *B01J 29/74* | (2006.01) |
| *B01J 35/02* | (2006.01) |
| *C07C 409/14* | (2006.01) |
| *B01J 37/02* | (2006.01) |
| *B01J 35/10* | (2006.01) |

(52) U.S. Cl.
CPC .............. *C07C 2/74* (2013.01); *B01J 29/7476* (2013.01); *B01J 35/0006* (2013.01); *B01J 35/008* (2013.01); *B01J 35/0073* (2013.01); *B01J 35/026* (2013.01); *B01J 37/02* (2013.01); *C07C 37/08* (2013.01); *C07C 45/53* (2013.01); *C07C 407/00* (2013.01); *C07C 409/14* (2013.01); *B01J 35/1019* (2013.01); *B01J 37/0009* (2013.01); *B01J 37/0201* (2013.01); *B01J 37/0223* (2013.01); *B01J 2229/20* (2013.01); *B01J 2229/42* (2013.01); *C07C 2101/14* (2013.01); *C07C 2521/04* (2013.01); *C07C 2521/06* (2013.01); *C07C 2521/08* (2013.01); *C07C 2529/74* (2013.01); *Y02P 20/52* (2015.11)

(58) Field of Classification Search
CPC ......... C07C 45/53; C07C 37/08; C07C 2/66; C07C 2/74; B01J 35/00
USPC ................ 568/342, 357, 798; 585/268, 467; 502/66
See application file for complete search history.

(56) References Cited

U.S. PATENT DOCUMENTS

| | | |
|---|---|---|
| 3,760,017 A | 9/1973 | Arkell et al. |
| 3,760,018 A | 9/1973 | Suggitt et al. |

(Continued)

FOREIGN PATENT DOCUMENTS

| | | |
|---|---|---|
| CN | 101687728 | 5/2013 |
| EP | 0 338 734 | 7/1992 |

(Continued)

OTHER PUBLICATIONS

Slaugh et al., "Hydrodimerization of Benzene to Phenylcyclohexane over Supported Transition Metal Catalysts" Journal of Catalysis, 1969, vol. 13, pp. 385-396.

(Continued)

*Primary Examiner* — Sikarl Witherspoon
(74) *Attorney, Agent, or Firm* — Stephen A. Baehl

(57) ABSTRACT

A process for producing an alkylated aromatic compound comprises contacting an aromatic starting material and hydrogen with a plurality of catalyst particles under hydroalkylation conditions to produce an effluent comprising the alkylated aromatic compound, the catalyst comprising a composite of a solid acid, an inorganic oxide different from the solid acid and a hydrogenation metal, wherein the distribution of the hydrogenation metal in at least 60 wt % of the catalyst particles is such that the average concentration of the hydrogenation metal in the rim portion of a given catalyst particle is Crim, the average concentration of the hydrogenation metal in the outer portion of a given catalyst particle is Couter, the average concentration of the hydrogenation metal in the center portion of the given catalyst particle is Ccenter, where Crim/Ccenter≥2.0 and/or Couter/Ccenter≥2.0. Also disclosed are rimmed catalyst and process for making phenol and/or cyclohexanone using the catalyst.

25 Claims, 3 Drawing Sheets

(56) References Cited

U.S. PATENT DOCUMENTS

| | | | |
|---|---|---|---|
| 4,268,699 | A | 5/1981 | Murtha et al. |
| 4,329,531 | A | 5/1982 | Murtha et al. |
| 4,439,409 | A | 3/1984 | Puppe et al. |
| 4,826,667 | A | 5/1989 | Zones et al. |
| 4,954,325 | A | 9/1990 | Rubin et al. |
| 5,053,571 | A | 10/1991 | Makkee |
| 5,146,024 | A | 9/1992 | Reed |
| 5,236,575 | A | 8/1993 | Bennett et al. |
| 5,250,277 | A | 10/1993 | Kresge et al. |
| 5,362,697 | A | 11/1994 | Fung et al. |
| 6,037,513 | A | 3/2000 | Chang et al. |
| 6,077,498 | A | 6/2000 | Diaz Cabanas et al. |
| 6,303,530 | B1 | 10/2001 | Schwartz et al. |
| 6,756,030 | B1 | 6/2004 | Rohde et al. |
| 7,906,685 | B2 | 3/2011 | Chen et al. |
| 7,910,778 | B2 | 3/2011 | Chen et al. |
| 2010/0191017 | A1* | 7/2010 | Chen ............... C07C 2/74 568/357 |
| 2012/0178969 | A1 | 7/2012 | Cheng et al. |

FOREIGN PATENT DOCUMENTS

| | | |
|---|---|---|
| EP | 0 293 032 | 7/1993 |
| EP | 2 080 746 | 7/2009 |
| WO | 97/17290 | 5/1997 |
| WO | 2009/021604 | 2/2009 |
| WO | 2009/038900 | 3/2009 |
| WO | 2011/096995 | 8/2011 |
| WO | 2012/050751 | 4/2012 |
| WO | 2014/159100 | 10/2014 |

OTHER PUBLICATIONS

G.N. Koshel et al., "Single-step method for hydrodimerization of benzene to phenylcyclohexane and some industrial syntheses based thereon" Doklady Akademii Nauk SSR 237 (1977) pp. 164-167. (Translation).

* cited by examiner

PROCESS FOR MAKING ALKYLATED AROMATIC COMPOUND

PRIORITY CLAIM TO RELATED APPLICATIONS

This application is a National Stage Application of International Application No. PCT/US2014/021235 filed Mar. 6, 2014, which claims priority to U.S. Provisional Application Ser. No. 61/804,957 filed Mar. 25, 2013, and European Application No. 13172273.8 filed Jun. 17, 2013, the disclosures of which are fully incorporated herein by their reference.

FIELD

The present invention relates to processes for making alkylated aromatic compounds by hydroalkylation. In particular, the present invention relates to processes for producing cyclohexylbenzene by hydroalkylating benzene in the presence of a catalyst. The present invention is useful, e.g., in producing phenol and cyclohexanone starting from hydroalkylation of benzene.

BACKGROUND

Phenol is an important product in the chemical industry and is useful in, for example, the production of phenolic resins, bisphenol A, ε-caprolactam, adipic acid, plasticizers, and polymers such as nylon-6.

Currently, a common route for the production of phenol is the Hock process via cumene. This is a three-step process in which the first step involves alkylation of benzene with propylene in the presence of an acidic catalyst to produce cumene. The second step is oxidation, preferably aerobic oxidation, of cumene to the corresponding cumene hydroperoxide. The third step is the cleavage of the cumene hydroperoxide in the presence of heterogeneous or homogeneous catalysts into equimolar amounts of phenol and acetone, a co-product. However, the world demand for phenol is growing more rapidly than that for the acetone co-product. This imbalance depresses the value of the co-product reducing the economic benefits of the Hock process.

Thus, a process that coproduces higher ketones, rather than acetone, may be an attractive alternative route to the production of phenol. In addition, there is a growing market for cyclohexanone, which is used as an industrial solvent, as an activator in oxidation reactions and in the production of adipic acid, cyclohexanone resins, cyclohexanone oxime, caprolactam, and nylon-6.

As it has been recently disclosed, phenol and cyclohexanone can be co-produced by a novel process in which cyclohexylbenzene is oxidized to obtain cyclohexylbenzene hydroperoxide, which, in turn, is decomposed in the presence of an acid catalyst to the desired phenol and cyclohexanone in a cleavage process.

Although the production of phenol and cyclohexanone from cyclohexylbenzene appears to be analogous to the Hock process for producing phenol and acetone from cumene, the chemistries in each step are actually very different.

It is known from U.S. Pat. Nos. 5,053,571 and 5,146,024 that cyclohexylbenzene can be produced by contacting benzene with hydrogen in the presence of a catalyst comprising ruthenium and nickel supported on zeolite beta and that the resultant cyclohexylbenzene can be processed in two steps to cyclohexanone and phenol. U.S. Pat. No. 6,037,513 discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt and mixtures thereof. The catalyst also contains a binder and/or matrix and in the Examples the catalyst is produced by impregnating an extrudate of the MCM-22 family molecular sieve and an alumina binder with an aqueous solution of a salt of the hydrogenation metal using incipient wetness impregnation. The '513 patent also discloses that the resultant cyclohexylbenzene can be oxidized to the corresponding hydroperoxide and the peroxide decomposed to the desired phenol and cyclohexanone.

SUMMARY

According to the present disclosure, a hydroalkylation catalyst for making an alkylated aromatic compound such as cyclohexylbenzene comprising a solid acid such as a molecular sieve, an inorganic oxide different from the solid acid and a hydrogenation metal and exhibiting a significantly higher concentration of the hydrogenation metal in the rim portion and/or outer portion compared to the center portion of the catalyst particles demonstrated very high benzene conversion and cyclohexylbenzene and dicyclohexylbenzene selectivity. Given that such rimmed hydrogenation metal distribution may require shorter diffusion time of the reactant in the hydroalkylation reaction, this catalyst can have better monoalkylation selectivity and improve the yield of the desired cyclohexylbenzene product.

A first aspect of the present disclosure relates to a process for producing an alkylated aromatic compound, the process comprising contacting an aromatic starting material and hydrogen with a plurality of catalyst particles under hydroalkylation conditions to produce an effluent comprising the alkylated aromatic compound, the catalyst comprising a composite of a solid acid, an inorganic oxide different from the solid acid and a hydrogenation metal, wherein the distribution of the hydrogenation metal in at least 60 wt % of the catalyst particles is such that:

the average concentration of the hydrogenation metal in the rim portion of a given catalyst particle is $C_{rim}$;

the average concentration of the hydrogenation metal in the outer portion of a given catalyst particle is $C_{outer}$; and the average concentration of the hydrogenation metal in the center portion of the given catalyst particle is $C_{center}$;

where at least one of the following conditions is met:

(i) $C_{rim}/C_{center} \geq 2.0$; and (ii) $C_{outer}/C_{center} \geq 2.0$.

A second aspect of the present disclosure relates to a process for making phenol and/or cyclohexanone, the process comprising:

(1) producing cyclohexylbenzene using a process according to the first aspect;

(2) oxidizing at least a portion of the cyclohexylbenzene to produce cyclohexylbenzene hydroperoxide; and (3) cleaving at least a portion of the cyclohexylbenzene hydroperoxide to obtain phenol and cyclohexanone.

A third aspect of the present disclosure relates to a catalyst, the catalyst comprising a composite of a solid acid, an inorganic oxide different from the solid acid and a hydrogenation metal, wherein the distribution of the hydrogenation metal in at least 60 wt % of the catalyst particles is such that:

the average concentration of the hydrogenation metal in the rim portion of a given catalyst particle is Crim;

the average concentration of the hydrogenation metal in the outer portion of a given catalyst particle is Couter; and the average concentration of the hydrogenation metal in the center portion of the given catalyst particle is Ccenter;

where at least one of the following conditions is met:

(i) Crim/Ccenter≧2.0; and (ii) Couter/Ccenter≧2.0.

Additional features and advantages of the invention will be set forth in the detailed description and claims, as well as the appended drawings. It is to be understood that the foregoing general description and the following detailed description are merely exemplary of the invention, and are intended to provide an overview or framework to understanding the nature and character of the invention as it is claimed.

DETAILED DESCRIPTION

Figure 1:
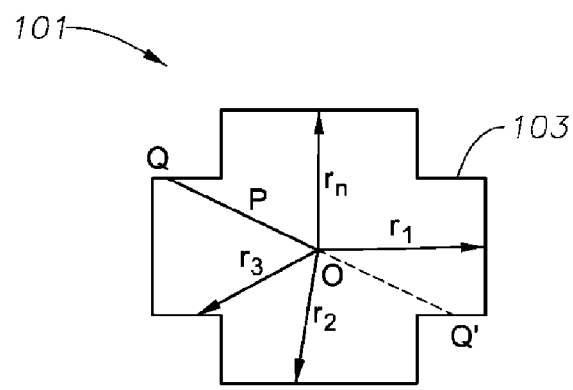
FIG. 1 is a schematic illustration of the cross-section of a catalyst particle in one embodiment of the present disclosure.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as listed, with or without overlapping with one or more other step, or in any other order, as the case may be. In addition, one or more, or even all steps, may be conducted simultaneously with regard to the same or different batch of material(s). For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenation metal" include embodiments where one, two, or more different types of the hydrogenation metals are used, unless specified to the contrary or the context clearly indicates that only one type of the hydrogenation metal is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

As used herein, the term "methylcyclopentanone" includes both isomers 2-methylcyclopentanone (CAS Registry No. 1120-72-5) and 3-methylcyclopentanone (CAS Registry No. 1757-42-2), at any proportion between them, unless it is clearly specified to mean only one of these two isomers or the context clearly indicates that is the case. It should be noted that under the conditions of the various steps of the present processes, the two isomers may undergo isomerization reactions to result in a ratio between them different from that in the raw materials immediately before being charged into a vessel such as a fractionation column.

As used herein, the generic term "dicylcohexylbenzene" ("DiCHB") includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in the singular form, means mono substituted cyclohexylbenzene. As used herein, the term "C12" means compounds having 12 carbon atoms, and "C12+ components" means compounds having at least 12 carbon atoms. Examples of C12+ components include, among others, cyclohexylbenzene, biphenyl, bicyclohexane, methylcyclopentylbenzene, 1,2-biphenylbenzene, 1,3-biphenylbenzene, 1,4-biphenylbenzene, 1,2,3-triphenylbenzene, 1,2,4-triphenylbenzene, 1,3,5-triphenylbenzene, and corresponding oxygenates such as alcohols, ketones, acids, and esters derived from these compounds. As used herein, the term "C18" means compounds having 18 carbon atoms, and the term "C18+ components" means compounds having at least 18 carbon atoms. Examples of C18+ components include, among others, diicyclohexylbenzenes ("DiCHB," described above), tricyclohexylbenzenes ("TriCHB," including all isomers thereof, including 1,2,3-tricyclohexylbenzene, 1,2,4-tricyclohexylbenzene, 1,3,5-tricyclohexylbenzene, and mixtures of two or more thereof at any proportion). As used herein, the term "C24" means compounds having 24 carbon atoms.

The term "MCM-22 type material" (or "material of the MCM-22 type" or "molecular sieve of the MCM-22 type" or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purpose of the present disclosure. Desirably, the molecular sieve used in the catalyst of the present disclosure is selected from (a) MCM-49; (b) MCM-56; and (c) isotypes of MCM-49 and MCM-56, such as ITQ-2.

Hydroalkylation catalysts can be used in various reactors, such as fixed, ebullating, or fluidized bed, or slurry reactors. Fixed beds are often preferred due to their lower cost operation and easier reaction medium/catalyst separation. For fixed bed applications, practical catalysts are typically shaped into extrudates or pellets for ensuring low flow resistance through the catalyst bed and for good contact between the catalyst and the reaction medium. The extrudates may have round or other solid cross-sectional profiles, but they may even be tubular. To increase the outside surface area and to reduce the average diffusion path length of the reactants and products at a given overall cross sectional area of a rod-like solid extrudate, the shape of the cross section often has multiple lobes. For example, a quadralobe extrudate has four lobes, which can be considered as protrusions on a round core.

The catalyst disclosed herein is in solid state under use conditions. The catalyst material in use may exhibit multiple or a single geometry and size. Thus, the catalyst may manifest itself as pellets, powders, or monolithic bodies. For the convenience of description herein, these different solid manifestations are connectively called "particles," regardless of their actual sizes, which may range from nanoscopic to macroscopic scales. For the convenience of description, the term "particle" is also used interchangeably with the term "pellet" herein. For each particle or pellet, there is a hypothetical three-dimensional rectangular cuboid capable of containing the particle having three dimensions a, b, and c, where a≥b≥c, with the smallest possible volume. The longest dimension of the rectangular cuboid, a, is called the longest axis of the particle.

Figure 2A:
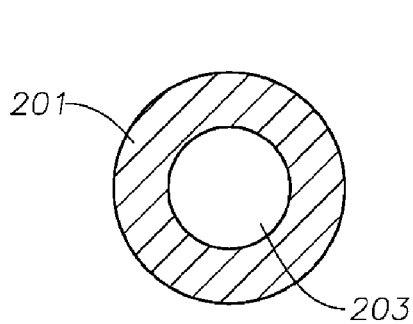
FIGS. 2A and 2B are schematic illustrations of cross-sections of catalyst particles in additional embodiments of the present disclosure.
Figure 2B:
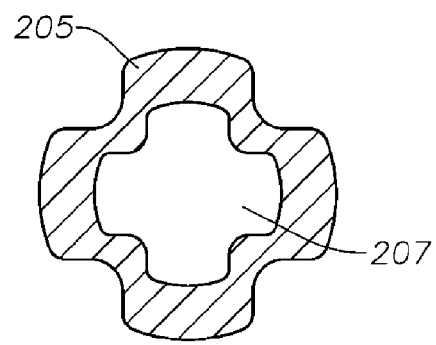
Figures 3A, 3B, 3C:
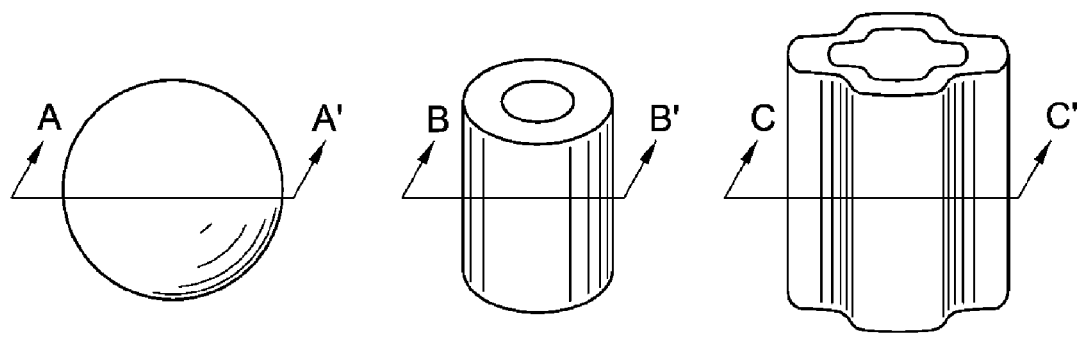
FIGS. 3A, 3B, and 3C are schematic illustrations of catalyst particles and directions in which cross-sections may be taken.

The cross-section of the catalyst particle is taken by intersecting the particle by a plane perpendicular to its longest axis, a. For a spherical particle shown in FIG. 3A, the cross-section would be a circle perpendicular to any diameter thereof taken in the direction of AA'. For a cylindrical particle having a height larger that its diameter, such as one illustrated in FIG. 3B, the cross-section can be taken in the direction of BB' and would be a circle having a radius of the cylinder perpendicular to the axis of the cylinder, shown in FIG. 2A. For a cubic particle, the cross-section can be any of the planes that runs parallel with one of the faces of the cube and runs through the center of the cube. Unisothropical shapes, often made by extrusion in the art of catalyst manufacturing, may have many types of cross-sections that could be, for example, round forming a cylinder, or lobed rectangles or circles forming cylinders of increased surface area, etc. Most typically these catalyst particles have the characteristic of a "noodle-like" shape with a longest axis and various cross-sectional shapes that can be taken in the direction CC', and a/b>1, where a and b are defined above, such as one illustrated in FIG. 3C. For the purpose of characterizing metal distribution in the cross-section in the present disclosure, the cross-section of these catalyst particles, schematically illustrated in FIG. 2B, would be a cut perpendicular to its longest axis anywhere along that axis as long as the cut is made at a distance of at least 0.5×b from either end of the extrudate, where b is defined above. Thus, for example, in the case of a round cross-section of an ideal cylinder catalyst particle, b would be equal to the diameter of the cross-section.

For a solid particle, the cross-section would be a continuous area bounded by an outer perimeter without an inner boundary. For a hollow particle, the cross-section can be a continuous area defined by an outer boundary and at least one inner boundary.

Referring to FIG. 1, the definition of the center of a cross-section O is given as follows.

Any given point (P) inside the area bounded by the outer perimeter 103 of the cross-section 101 has distances of $r_1$, $r_2$, $r_3$, . . . , and $r_n$, to the different points on the perimeter of the cross-section. The average mean square distance is calculated as:

$$r_{ms} = \frac{\sqrt{r_1^2 + r_2^2 + r_3^2 + \ldots + r_n^2}}{n}.$$

The center (O) of the cross-section is the point inside the outer perimeter having the smallest average mean square distance $r_{ms}$ to the outer perimeter. For a centrally symmetrical cross-section, the center would be the center of symmetry, such as the center of a circle, an elliptical, a square, or a rectangle.

For any given point P inside the outer perimeter, draw a straight line passing both points O and P. The line intersects the outer perimeter at points Q and Q' such that P is located between Q and O. The length of the segment between points Q and O is |QO|, and the length of the segment between points P and O is |PO|. Note that for all possible choices of P, i.e., for all points within the cross-section, |PQ|≤|QO|. Using these definitions, the rim portion, the outer portion, and the center portion of a cross-section can be given as follows:

The rim portion of the cross-section is defined as the area occupied by all possible points P for which |PQ|/|QO|≤0.20. For a circular cross-section having a radius $r_0$, the rim portion would be the ring bounded by the outer perimeter of the cross-section and a concentric circle having a radius of $0.8 \cdot r_0$.

The "outer portion" of the cross-section is defined as the area occupied by all possible points for which |PQ|/|QO|≤0.30. For a circular cross-section having a radius $r_0$, the outer portion would be the ring bounded by the outer perimeter of the cross-section and a concentric circle having a radius of $0.7 \cdot r_0$.

The center portion of the cross-section is defined as the portion occupied by all points P for which |PO|/|QO|≤0.10. Thus, the center portion of the cross-section shares a common center O with the entire cross-section. For a circular cross-section having a radius $r_0$, the center portion would be a concentric circle having a radius of $0.1 \cdot r_0$. In general, the center portion of the cross-section has the same or similar shape as the entire cross-section and can be enlarged to overlap with the full cross-section without rotating it around its center.

For a given catalyst particle cross-section, the concentration of a given metal, such as Pd, may be measured using known methods such a EPMA analysis. The average concentration in the rim portion is Crim, and the average concentration in the center portion is Ccenter. As used herein, a "rimmed catalyst" is a catalyst exhibiting Crim/Ccenter>1.0, i.e., that which exhibits a higher average concentration in the rim portion than in the center portion.

Hydroalkylation converts aromatic hydrocarbons, such as benzene, substituted benzenes, such as toluene, ethylbenzene, cumene, cyclohexylbenzene, xylenes, etc., naphthalene, substituted naphthalenes and the like, and hydrogen to alkyl-aromatic compounds, in which the aromatic component of the feed is substituted by an alkyl component derived by the partial hydrogenation of the same aromatic feed component. An example of such process is the hydroalkylation of benzene to cyclohexylbenzene (CHB).

The catalyst used in the present disclosure is characterized in the preferential distribution of the hydrogenation metal in the rim portion and/or outer portion compared to the center portion of a majority of the catalyst particles. The catalyst particles comprise a composite of a solid acid, an inorganic oxide different from the solid acid and a hydrogenation metal, and the distribution of the hydrogenation metal in at least 60 wt % (or at least aa wt %, where aa can be: 65, 70, 75, 80, 85, 90, 95, 98, or even 99) of the catalyst particles is such that the average concentration of the hydrogenation metal in the rim portion of a given catalyst particle is Crim, the average concentration of the hydrogenation metal in the outer portion of a given catalyst particle is Couter, the average concentration of the hydrogenation metal in the center portion of the given catalyst particle is Ccenter, where Crim/Ccenter≥2.0 and/or Couter/Ccenter≥2.0. In certain embodiments, at least one of the following conditions s met: (i) X≤Crim/Ccenter≤Y; and (ii) X≤Couter/Ccenter≤Y, where X can be: 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35.0, 40.0, 45.0, 50.0, 60.0, 70.0, 80.0, 90.0, or even 100.0; and Y can be: 50000, 20000, 10000, 8000, 5000, 3000, 2000, 1000, 900, 800, 700, 600, 500, 400, 300, 200, 180, 160, 150, 140, 130, 120, 110, 100, 90.0, 80.0, 70.0, 60.0, or even 50.0, as long as X<Y.

The solid acid component in the composite of the catalyst of the present disclosure provides at least a portion of the alkylation function of the catalyst. The solid acid can be, e.g., a molecular sieve, amorphous silica-alumina, or mixed metal oxides such as tungstated zirconia, or other suitable solid acid known in the art. Suitable solid acid molecular sieves include but are not limited to: mordenite, zeolite X, Y, beta, molecular sieves of the MWW type, such as those in the MCM-22 type as described above. Examples of MWW type molecular sieves that can be advantageously used in the catalyst of the present disclosure include but are not limited to: MCM-22, PSH-3, SSZ-25, ERB-1, ITQ-1, ITQ-2, MCM-36, MCM-49, and MCM-56.

The inorganic oxide different from the molecular sieve contained in the catalyst of the present disclosure can provide multiple functions such as (i) binding the molecular sieve particles together to form a larger particle such as a pellet or other monolithic body; (ii) supporting the hydrogenation metal in the catalyst particle; and (iii) optionally providing acidic locations capable of catalyzing the alkylation reactions. Thus, the inorganic oxide may comprise one or more of the following: silica; alumina; zirconia; titania, and oxides of other metals in Group 2, 3, 4, 5, 6, 7, 13, and 14 of the Periodic Table of Elements. The amount of the inorganic oxide different from the solid acid present in the catalyst particle may vary. For example, the weight ratio of the solid acid to the inorganic oxide different from the solid acid can range from R1 to R2, where R1 can be 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0; and R2 can be 8.0, 7.5, 7.0, 6.5, 6.0, 5.5, 5.0, 4.9, 4.8, 4.7, 4.6, 4.5, 4.4, 4.3, 4.2, 4.1, 4.0, 3.5, 3.0, 2.5, 2.0, as long as R1<R2. In one example, the weight ratio of the solid acid to the inorganic oxide different from the solid acid is about 4.0, which was found to be particularly advantageous for a catalyst comprising a MWW type molecular sieve (the solid acid) and $Al_2O_3$ binder (the inorganic oxide different from the solid acid).

The catalyst used in the process of the present disclosure may comprise a promoter, such as a metal selected from Groups 1, 2, 13 and 14 of the Periodic Table of Elements, Zn, halogens, and the like.

The hydrogenation metal catalyzes the hydrogenation of at least a part of the feed material to produce an alkylating agent (e.g., an olefin) during the hydroalkylation process, which, in turn, reacts with part of the feed material to produce the desired alkylated aromatic compound. The hydrogenation metal is advantageously selected from Groups 8-10 metals of the Periodic Table of Elements, and mixtures and combinations thereof. Particularly advantageous hydrogenation metal is selected from: Fe, Co, Ni, Ru, Th, Pd, Os, Ir, Pt, Zr, and mixtures and combinations thereof. The amount of the hydrogenation metal present in the catalyst particles can vary. For example, the weight percentage of the hydrogenation metal, expressed on the basis of metallic metal, relative to the total weight of the catalyst particle, can be in the range from A1% to A2%, where A1 can be 0.001, 0.005, 0.01, 0.05, 0.10, 0.15, 0.20, 0.25, 0.30, 0.35, 0.40, 0.45, 0.50, 0.60, 0.70, 0.80, 0.90, 1.00; and A2 can be 10.00, 8.00, 5.00, 4.00, 3.00, 2.00, 1.50, 1.40, 1.30, 1.20, 1.10, 1.00, 0.90, 0.80, 0.70, 0.60, 0.50, 0.40, 0.30, 0.20, or 0.10, as long as A1<A2. Where a precious metal such as Pd, Pt, Ru, Rh, Ir, and the like, is used, it is desirable that they are used as a relatively low concentration due to high cost.

It is believed that to provide desired level of hydrogenation function, the hydrogenation metal contained in the catalyst of the present disclosure is advantageously in an oxidation state of zero. Thus, in the catalyst particles used in the present disclosure, at least x % of the hydrogenation metal is in zero oxidation state, where x can be: 80, 82, 84, 85, 86, 88, 90, 92, 94, 95, 96, 98, 99, or even 99.5.

In certain embodiments of the catalyst of the present disclosure, at least AA wt % of the hydrogenation metal is supported on the inorganic oxide, where AA can be: 50, 55, 60, 65, 70, 75, 80, 85, 90, or even 95. It was found that the preferential distribution of the hydrogenation metal on the inorganic oxide compared to the surface of the molecular sieve would result in better performance of the catalyst in the hydroalkylation reaction. In certain embodiments, the inorganic oxide is present in the composite in the form of islets, and the islets are substantially uniformly distributed within the composite. In certain embodiments, it is desired that the islets of the inorganic oxide in the catalyst particle have an average size of BB micrometers, where $x \leq BB \leq y$, where x can be: 1, 2, 3, 4, 5, 6, 7, 8, 9, 10, 12, 14, 15, 16, 18, 20, 22, 24, 25, 26, 28, 30, and y can be: 40, 38, 36, 35, 34, 32, 30, 28, 26, 25, 24, 22, 20, 18, 16, 15, 14, 12, or 10, as long as x<y.

In one embodiment, the catalyst particles are made by a catalyst fabrication process comprising: (I) forming a mixture comprising the solid acid and the inorganic oxide; (II) forming a pellet form the mixture; (III) depositing a source material of the hydrogenation metal onto the pellet; and (IV) calcining the pellet after step (III) at a temperature in the range from 400° C. to 1000° C. In specific embodiments, the catalyst fabrication process further comprises, after step (IV): (V) activating the calcined pellet in the presence of an atmosphere comprising $H_2$. In more specific embodiments, in step (III), the source material of the hydrogenation metal comprises $PdCl_2$, and step (II) comprises impregnating the pellet with an aqueous $PdCl_2$ dispersion having a pH in the range from 0 to 4.

The particles such as pellets can be formed by using methods such as extrusion, molding, casting, and the like. Complex particle geometry and various sizes can be achieved using forming methods known in the art. For example, extrusion can be used to form "noodle-like" pellets, which may be further optionally diced to obtain the pellets with desired sizes.

The source material of the hydrogenation metal can be advantageously a salt of the metal, which can be present in a liquid dispersion such as an aqueous solution, an emulsification, or a suspension. Advantageously, the distribution of the salt material in the dispersion is substantially uniform, which would desirably result in a substantially uniform distribution thereof on the surface of the relevant particles at the end of the depositing step. The liquid dispersion may advantageously comprise other components than a solvent and the source material such as a pH modifier. For example, a $PdCl_2$ solution may advantageously comprise HCl such that the pH of the solution is from 0 to 4. This pH range was found to be particularly beneficial for a uniform deposition of $PdCl_2$ on the surface of the relevant particles. The deposition can be effected by impregnating the particles with the dispersion, spraying the dispersion to the particles, and the like.

To achieve preferential distribution of the hydrogenation metal in the rim portion and/or outer portion compared to the center portion of the catalyst pellet, it is highly desired that in the deposition step, the source material is deposited preferentially to the rim portion and/or outer portion of the particle prior to calcination. To that end, one can adjust the method of deposition, such as the amount of the dispersion used, and contact time between the dispersion and the particle, the temperature of the dispersion and the particle during deposition, the rotating speed of the particles during deposition, and the like, so that the rim portion and/or outer portion thereof is wetted to a greater extent than the center portion by the dispersion of the source material of the hydrogenation metal in the depositing step. At the end of the depositing step, the as-formed particles prior to calcination may comprise, in addition to the inorganic oxide and/or the solid acid, and/or the source material of the hydrogenation metal, additional materials such as organic binders, surfactants, and the like. The as-formed particles may be dried prior to calcination, at a temperature in the range from Ta ° C. to Tb ° C., where Ta can be 0, 5, 10, 15, 20, 25, 30, 35, 40, 45, 50, 55, 60, 65, 70, 75, 80, 85, 90, 95, or 100; and Tb can be 200, 195, 190, 185, 180, 175, 170, 165, 160, 155, 150, 145, 140, 135, 130, 125, 120, 115, 110, 105, or 100, as long as Ta<Tb. Such drying can be advantageously conduced in air.

The calcining step is advantageously a high-temperature treatment carried out in the presence of an $O_2$-containing gas such as air. In this step, organic materials contained in the relevant particles are reduced or eliminated, water and/or other solvents are driven off, the particles are dried, and the hydrogenation metal is redistributed on the surface and at least part of the bulk of the particles. Calcination can be carried out at a temperature in a range from T1° C. to T2° C., where T1 can be: 300, 350, 400, 450, 500, 550, 600, 650, 700, 750, 800; and T2 can be: 1000, 950, 900, 850, 800, 750, 700, 650, 600, 550, 500, 450, and 400, as long as T1<T2.

Upon calcination, the hydrogenation metal is normally present on/in the particles at least partly at an oxidation state higher than zero. Thus, for example, where $PdCl_2$ is the source material of Pd, upon deposition and calcination, the Pd metal may be present in the form of $PdCl_2$, PdO, and the like, on or in the particle. Without intending to be bound by a particular theory, it is believed that the hydrogenation metal is desired to be at zero oxidation state when in active form for catalyzing the hydrogenation reaction. Thus, it is desired that in certain embodiments, after the final calcination of the catalyst particles and prior to use, the particles are subjected to a step of activation, where they are heated in a reducing atmosphere, such as a $H_2$-containing atmosphere, e.g., pure $H_2$, $H_2/N_2$ mixture, $H_2/CH_4$ mixture, $H_2/CH_4/N_2$ mixture, and the like. Desirably, the reducing atmosphere is a flowing stream of gas. Desirably, the reducing atmosphere comprises water at a concentration of at most A wt % (based on the total weight of the reducing atmosphere), where A can be 1.0, 0.1, 0.01, 0.005, 0.001, 0.0005, 0.0001, 0.00005, or even 0.00001, so that the catalyst particles are dried and purged of water produced during the activation step, if any. After this step, the oxidation state of at least a great majority, such as at least X %, where X can be 70, 75, 80, 85, 90, 95, 98, 99, or even 99.9, of the hydrogenation metal is zero. The activated catalyst may then be protected by an inert atmosphere or reducing atmosphere essentially free of $O_2$ before use in the hydroalkylation reaction, so that further oxidation thereof is prevented.

In the hydroalkylation reaction using the catalyst of the present disclosure, in addition to the desired alkylated aromatic product, by-products may be produced. For example, the aromatic feed material may be overly hydrogenated to yield an aliphatic compound. In the case of benzene hydroalkylation, benzene may be hydrogenated to form cyclohexane. The aliphatic compound (e.g., cyclohexane) is desirably dehydrogenated to form the aromatic compound feed, which is recycled to the hydroalkylation process, so as to increase the overall yield of the alkylated aromatic compound product. The alkylated aromatic compound can then be used to make various products. For example, cyclohexylbenzene, as a desired product of benzene hydroalkylation, may be oxidized to form hydroperoxide thereof, which is then subject to a cleavage reaction to make phenol and cyclohexanone.

The alkylation process may result in multiple products at various amounts, e.g., mono-, di-, and tri-alkylated aromatic compounds, and the like. Depending on the end application, one of more of these products may be the desired target compounds. For example, benzene hydroalkylation may produce mono-cyclohexylbenzene, DiCHB (including the various isomers described above), and TriCHB (including the various isomers described above). Thus, the processes and catalyst of the present disclosure may be used for making one or more of these products. Where mono-alkylated product such as mono-cyclohexylbenzene is the only desired target product, the DiCHB and TriCHB may be subjected to transalkylation in the presence of a transalkylation catalyst such as a solid acid (e.g., faujasite), where DiCHB reacts with benzene to produce mono-cyclohexylbenzene, and TriCHB reacts with benzene to produce mono-cyclohexylbenzene and DiCHB.

The present invention is particularly useful in making cyclohexylbenzene by benzene hydroalkylation. The cyclohexylbenzene can then by oxidized to a hydroperoxide thereof, which is then subjected to cleavage to make phenol and cyclohexanone. The following is a detailed description of this embodiment.

Supply of Cyclohexylbenzene

The cyclohexylbenzene supplied to the oxidation step can be produced and/or recycled as part of an integrated process for producing phenol and cyclohexanone from benzene. In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction-1 to produce cyclohexylbenzene (CHB):

(Reaction-1).

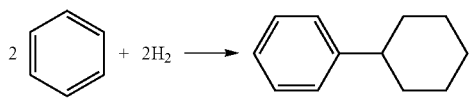

Alternatively, cyclohexylbenzene can be produced by direct alkylation of benzene with cyclohexene in the presence of a solid-acid catalyst such as molecular sieves in the MCM-22 family according to the following Reaction-2:

(Reaction-2).

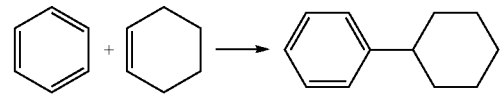

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

The catalyst employed in the hydroalkylation reaction is a bifunctional catalyst comprising a molecular sieve, such as one of the MCM-22 type described above and a hydrogenation metal.

Any known hydrogenation metal may be employed in the hydroalkylation catalyst, specific, non-limiting, suitable examples of which include Pd, Pt, Rh, Ru, Ir, Ni, Zn, Sn, Co, with Pd being particularly advantageous. Desirably, the amount of hydrogenation metal present in the catalyst is from 0.05 wt % to 10.0 wt %, such as from 0.10 wt % and 5.0 wt %, of the total weight of the catalyst.

In addition to the molecular sieve and the hydrogenation metal, the hydroalkylation catalyst may comprise one or more optional inorganic oxide support materials and/or binders. Suitable inorganic oxide support material(s) include, but are not limited to, clay, non-metal oxides, and/or metal oxides. Specific, non-limiting examples of such support materials include: $SiO_2$, $Al_2O_3$, $ZrO_2$, $Y_2O_3$, $Gd_2O_3$, SnO, $SnO_2$, and mixtures, combinations and complexes thereof.

The effluent from the hydroalkylation reaction (hydroalkylation reaction product mixture) or from the alkylation reaction (alkylation reaction product mixture) may contain some polyalkylated benzenes, such as dicyclohexylbenzenes (DiCHB), tricyclohexylbenzenes (TriCHB), methylcyclopentylbenzene, unreacted benzene, cyclohexane, bicyclohexane, biphenyl, and other contaminants. Thus, typically, after the reaction, the hydroalkylation reaction product mixture is separated by distillation to obtain a C6 fraction containing benzene, cyclohexane, a C12 fraction containing cyclohexylbenzene and methylcyclopentylbenzene, and a heavies fraction containing, e.g., C18s such as DiCHBs and C24s such as TriCHBs. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step.

Depending on the quantity of the heavies fraction, it may be desirable to either (a) transalkylate the C18s such as DiCHB and C24s such as TriCHB with additional benzene or (b) dealkylate the C18s and C24s to maximize the production of the desired monoalkylated species.

Transalkylation with additional benzene is desirably effected in a transalkylation reactor, which is separate from the hydroalkylation reactor, over a suitable transalkylation catalyst, such as a molecular sieve of the MCM-22 type, zeolite beta, MCM-68 (see U.S. Pat. No. 6,049,018), zeolite Y, zeolite USY, and mordenite. The transalkylation reaction is desirably conducted under at least partially liquid phase conditions, which suitably include a temperature in the range from 100° C. to 300° C., a pressure in the range from 800 kPa to 3500 kPa, a weight hourly space velocity from 1 hr$^{-1}$ to 10 hr$^{-1}$ on total feed, and a benzene/dicyclohexylbenzene weight ratio in a range from 1:1 to 5:1.

Dealkylation is also desirably effected in a reactor separate from the hydroalkylation reactor, such as a reactive distillation unit, at a temperature of about 150° C. to about 500° C. and a pressure in a range from 15 to 500 psig (200 to 3550 kPa) over an acid catalyst such as an aluminosilicate, an aluminophosphate, a silicoaluminophosphate, amorphous silica-alumina, an acidic clay, a mixed metal oxide, such as WO$_x$/ZrO$_2$, phosphoric acid, sulfated zirconia and mixtures thereof. Desirably, the acid catalyst includes at least one aluminosilicate, aluminophosphate or silicoaluminophosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction can be from 0 to about 0.9, such as from about 0.01 to about 0.5. Similarly, although the dealkylation reaction can be conducted in the absence of added hydrogen, hydrogen is desirably introduced into the dealkylation reactor to assist in coke reduction. Suitable hydrogen addition rates are such that the molar ratio of hydrogen to poly-alkylated aromatic compound in the total feed to the dealkylation reactor can be from about 0.01 to about 10.

The transalkylation or dealkylation product mixture comprising benzene, C12s and heavies can then be separated to obtain a C6 fraction, which comprises primarily benzene and can be recycled to the hydroalkylation/alkylation step, a C12s fraction comprising primarily cyclohexylbenzene, and a heavies fraction which can be subjected to a transalkylation/dealkylation reaction again or discarded.

The cyclohexylbenzene freshly produced and/or recycled may be purified before being fed to the oxidation step to remove at least a portion of, among others, methylcyclopentylbenzene, olefins, phenol, acid, and the like. Such purification may include, e.g., distillation, hydrogenation, caustic wash, and the like.

The cyclohexylbenzene feed to the oxidizing step may contain, based on the total weight of the feed, one or more of the following: (i) bicyclohexane at a concentration in a range from at 1 ppm to 1 wt %, such as from 10 ppm to 8000 ppm; (ii) biphenyl at a concentration in a range from 1 ppm to 1 wt %, such as from 10 ppm to 8000 ppm; (iii) water at a concentration up to 5000 ppm, such as from 100 ppm to 1000 ppm; and (iv) olefins or alkene benzenes, such as phenylcyclohexene, at a concentration no greater than 1000 ppm.

Oxidation of Cyclohexylbenzene

In the oxidation step, at least a portion of the cyclohexylbenzene contained in the oxidation feed is converted to cyclohexyl-1-phenyl-1-hydroperoxide, the desired hydroperoxide, according to the following Reaction-3:

(Reaction-3).

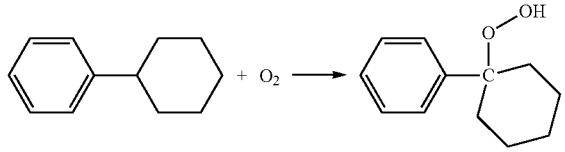

In exemplary processes, the oxidizing step may be accomplished by contacting an oxygen-containing gas, such as air and various derivatives of air, with the feed comprising cyclohexylbenzene. For example, a stream of pure O$_2$, O$_2$ diluted by inert gas such as N$_2$, pure air, or other O$_2$-containing mixtures can be pumped through the cyclohexylbenzene-containing feed in an oxidation reactor.

The oxidation may be conducted in the absence or presence of a catalyst. Examples of suitable oxidation catalysts include those having a structure of formula (FC-I), (FC-II), or (FC-III) below:

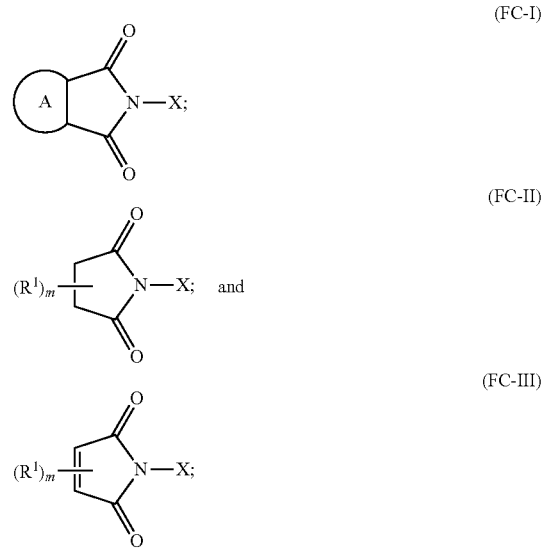

where:

A represents a ring optionally comprising a nitrogen, sulfur, or oxygen in the ring structure, and optionally substituted by an alkyl, an alkenyl, a halogen, or a N-, S-, or O-containing group or other group;

X represents a hydrogen, an oxygen free radical, a hydroxyl group, or a halogen;

R$^1$, the same or different at each occurrence, independently represents a halogen, a N-, S-, or O-containing group, or a linear or branched acyclic alkyl or cyclic alkyl group having 1 to 20 carbon atoms, optionally substituted by an alkyl, an alkenyl, a halogen, or a N-, S-, or O-containing group or other group; and m is 0, 1 or 2.

Examples of particularly suitable catalysts for the oxidation step include those represented by the following formula (FC-IV):

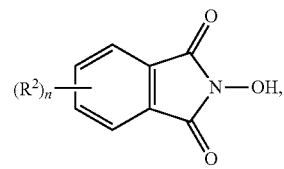

where:

R$^2$, the same or different at each occurrence, independently represents a halogen, a N-, S-, or O-containing group, or an optionally substituted linear or branched acyclic alkyl or cyclic alkyl group having 1 to 20 carbon atoms; and n is 0, 1, 2, 3, or 4.

One especially suitable catalyst having the above formula (FC-IV) for the oxidation step is NHPI (N-hydroxyphthalimide). For example, the feed to the oxidizing step can comprise from 10 to 2500 ppm of NHPI by weight of the cyclohexylbenzene in the feed.

Other non-limiting examples of the oxidation catalyst include: 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy (pyromellitic diimide), N,N'-dihydroxy(benzophenone-3,3', 4,4'-tetracarboxylic diimide), N-hydroxymaleimide, pyridine-2,3-dicarboximide, N-hydroxysuccinimide, N-hydroxy (tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, N-hydroxy-o-benzenedisulphonimide, and N,N',N"-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N"-trihydroxyisocyanuric acid is employed in an amount from 0.0001 wt % to 15 wt %, such as from 0.001 wt % to 5 wt %, of the cyclohexylbenzene feed.

Non-limiting examples of suitable reaction conditions of the oxidizing step include a temperature in a range from 70° C. to 200° C., such as 90° C. to 130° C., and a pressure in a range from 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an $O_2$-containing gas stream (such as air) through the media. For example, the oxidation reactor may comprise a simple, largely open vessel with a distributor inlet for the oxygen-containing gas stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series and/or in parallel, each operating at the same or different conditions selected to enhance the oxidation reaction in the reaction media with different compositions. The oxidation reactor may be operated in a batch, semi-batch, or continuous flow manner well known to those skilled in the art.

Composition of the Oxidation Reaction Product Mixture

Desirably, the oxidation reaction product mixture exiting the oxidation reactor contains cyclohexyl-1-phenyl-1-hydroperoxide at a concentration in a range from $Chp1$ wt % to $Chp2$ wt %, based on the total weight of the oxidation reaction product mixture, where $Chp1$ and $Chp2$ can be, independently, 5, 10, 15, 20, 25, 30, 35, 40, 45, 50, 55, 60, 65, 70, 75, 80, as long as $Chp1<Chp2$. Preferably, the concentration of cyclohexyl-1-phenyl-1-hydroperoxide in the oxidation reaction product mixture is at least 20% by weight of the oxidation reaction product mixture. The oxidation reaction product mixture may further comprise residual cyclohexylbenzene at a concentration in a range from $Cchb1$ wt % to $Cchb2$ wt %, based on the total weight of the oxidation reaction product mixture, where $Cchb1$ and $Cchb2$ can be, independently, 20, 25, 30, 35, 40, 45, 50, 55, 60, 65, 70, 75, 80, 85, 90, 95, as long as $Cchb1<Cchb2$. Preferably, the concentration of cyclohexylbenzene in the oxidation reaction product mixture is at most 65% by weight of the oxidation reaction product mixture.

In addition, the oxidation reaction product mixture may contain one or more hydroperoxides other than cyclohexyl-1-phenyl-1-hydroperoxide generated as byproduct(s) of the oxidation reaction of cyclohexylbenzene, or as the oxidation reaction product of oxidizable component(s) other than cyclohexylbenzene that may have been contained in the feed supplied to the oxidizing step, such as cyclohexyl-2-phenyl-1-hydroperoxide, cyclohexyl-3-phenyl-1-hydroperoxide, and methylcyclopentylbenzene hydroperoxides. These undesired hydroperoxides are present at a total concentration from $Cu1$ wt % to $Cu2$ wt %, where $Cu1$ and $Cu2$ can be, independently, 0.1, 0.2, 0.3, 0.5, 0.7, 0.9, 1.0, 1.2, 1.4, 1.5, 1.6, 1.8, 2.0, 2.5, 3.0, 3.5, 4.0, 4.5, 5.0, 6.0, 7.0, 8.0, as long as $Cu1<Cu2$. They are undesirable because they may not convert into phenol and cyclohexanone in the cleavage reaction at the desired conversion and/or selectivity, resulting in overall yield loss.

As noted above, the oxidation reaction product mixture may also contain phenol as a further by-product of the oxidation reaction. The concentration of phenol ($CPh$) in the oxidation reaction product mixture exiting the oxidation reactor(s) can range from $CPh1$ ppm to $CPh2$ ppm, where $CPh1$ and $CPh2$ can be, independently: 50, 60, 70, 80, 90, 100, 150, 200, 250, 300, 350, 400, 450, 500, 550, 600, 650, 700, 750, 800, 850, 900, 950, 1000, 1500, 2000, as long as $CPh1<CPh2$.

The oxidation reaction product mixture may contain water. The concentration of water in the oxidation reaction product mixture exiting the oxidation reactor may range from $C1a$ ppm to $C1b$ ppm, based on the total weight of the oxidation reaction product mixture, where $C1a$ and $C1b$ can be, independently: 30, 40, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, or 5000, as long as $C1a<C1b$.

The oxidation reaction product mixture may also contain part or all of any catalyst, such as NHPI, supplied to the oxidizing step. For example, the oxidation reaction product mixture may contain from 10 to 2500 ppm of NHPI, such as from 100 to 1500 ppm by weight of NHPI.

Treatment of the Oxidation Reaction Product Mixture

In the process of the present disclosure, before being supplied to the cleavage step, at least a portion of the oxidation reaction product mixture may be separated. The separation process may include subjecting at least a portion of the oxidation reaction product mixture to vacuum evaporation so as to recover: (i) a first fraction comprising the majority of the cyclohexyl-1-phenyl-1-hydroperoxide and other higher boiling components of the oxidation reaction product mixture portion, such as other hydroperoxides and NHPI catalyst, if present in the oxidation reaction product mixture portion; and (ii) a second fraction comprising a major portion of the cyclohexylbenzene, phenol, if any, and other lower boiling components of the oxidation reaction product mixture portion.

Desirably, in the first fraction, the concentration of cyclohexyl-1-phenyl-1-hydroperoxide can range from Cc1 wt % to Cc2 wt %, and the concentration of cyclohexylbenzene can range from Cd1 wt % to Cd2 wt %, based on the total weight of the first fraction, where Cc1 and Cc2 can be, independently, 40, 45, 50, 55, 60, 65, 70, 75, 80, 85, 90, as long as Cc1<Cc2; and Cd1 and Cd2 can be, independently, 10, 15, 20, 25, 30, 35, 40, 45, 50, as long as Cd1<Cd2.

Advantageously, in the second fraction, the concentration of cyclohexyl-1-phenyl-1-hydroperoxide can range from Cc3 wt % to Cc4 wt %, and the concentration of cyclohexylbenzene can range from Cd3 wt % to Cd4 wt %, based on the total weight of the second fraction, where Cc3 and Cc4 can be, independently, 0.01, 0.05, 0.10, 0.20, 0.40, 0.50, 0.60, 0.80, 1.00, 1.50, 2.00, 2.50, 3.00, 3.50, 4.00, 4.50, 5.00, as long as Cc3<Cc4; and Cd3 and Cd4 can be, independently, 90, 92, 94, 95, 96, 97, 98, or even 99, as long as Cd3<Cd4.

Because cyclohexylbenzene hydroperoxide is prone to decomposition at elevated temperatures, e.g., at above 150° C., the vacuum evaporation step to separate the oxidation reaction product mixture into the first and second fractions is conducted at a relatively low temperature, e.g., no higher than 130° C., or no higher than 120° C., or even no higher than 110° C. Cyclohexylbenzene has a high boiling point (239° C. at 101 kPa). Thus, at acceptable cyclohexylbenzene-removal temperatures, cyclohexylbenzene tends to have very low vapor pressure. Accordingly, preferably, to effectively remove a meaningful amount of cyclohexylbenzene from the oxidation reaction product mixture, the oxidation reaction product mixture is subjected to a very low absolute pressure, e.g., in a range from Pc1 kPa to Pc2 kPa, where Pc1 and Pc2 can be, independently, 0.05, 0.10, 0.15, 0.20, 0.25, 0.26, 0.30, 0.35, 0.40, 0.45, 0.50, 0.60, 0.65, 0.70, 0.75, 0.80, 0.85, 0.90, 0.95, 1.00, 1.50, 2.00, 2.50, 3.00, as long as Pc1<Pc2. Particularly advantageously, Pc1=0.25, and Pc2=1.5.

After separation of the oxidation reaction product mixture into the first and second fractions, part or all of the first fraction can be routed directly to the cleavage step. All or a portion of the first fraction may be cooled before passage to the cleavage step so as to cause crystallization of the unreacted imide oxidation catalyst. The imide crystals may then be recovered for reuse either by filtration or by scraping from a heat exchanger surface used to effect the crystallization.

The second fraction produced from the oxidation reaction product mixture may be treated to reduce the level of phenol therein before part or all of the cyclohexylbenzene in the second fraction is recycled to the hydrogenation.

Treatment of the second fraction can comprise contacting at least a portion of the second fraction with an aqueous composition comprising a base under conditions such that the base reacts with the phenol to produce a phenoate species which remains in the aqueous composition. A strong base, that is a base having a $pK_b$ value less than 3, such as less than 2, 1, 0, or −1, is desirably employed in the treatment of the second fraction. Particularly suitable bases include hydroxides of alkali metals (e.g., LiOH, NaOH, KOH, RbOH), hydroxides of alkaline earth metals ($Mg(OH)_2$, $Ca(OH)_2$, $Sr(OH)_2$, $Ba(OH)_2$), and mixtures of one or more thereof. Phenol can react with these hydroxides to form phenoates, which typically have higher solubility in water than phenol per se. A particularly desirable base is NaOH, which is cost efficient and capable of reacting with phenol in the second fraction to produce sodium phenoate. It should be noted that, when a hydroxide is used as the base, because of the reaction of $CO_2$ present in the atmosphere with the hydroxide, the aqueous composition may comprise, at various concentrations, one or more of a corresponding carbonate, bicarbonate, or carbonate-hydroxide complex. Desirably, the aqueous composition comprising the base has a pH of at least 8, preferably at least 10.

Contacting of the second fraction with the aqueous composition comprising a base produces an aqueous phase containing at least part of the phenol and/or a derivative thereof from the second fraction and an organic phase containing cyclohexylbenzene and having a reduced concentration of phenol as compared with the second fraction. Desirably, the phenol concentration in the organic phase is in the range from CPh7 ppm to CPh8 ppm, based on the total weight of the organic phase, where CPh7 and CPh8 can be, independently: 0, 10, 20, 30, 40, 50, 100, 150, 200, 250, as long as CPh7<CPh8.

The organic phase can then be separated from the aqueous phase, for example, spontaneously under gravity, and can then be recycled to the oxidizing step as a third fraction either directly, or more preferably, after water washing to remove base entrained in the organic phase.

Cleavage Reaction

In the cleavage reaction, at least a portion of the cyclohexyl-1-phenyl-1-hydroperoxide decomposes in the presence of an acid catalyst in high selectivity to cyclohexanone and phenol according to the following desired Reaction-4:

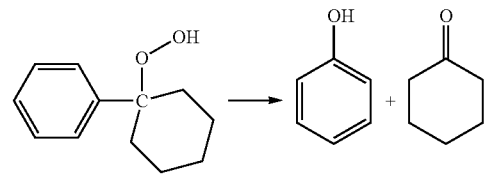

(Reaction-4).

The cleavage product mixture may comprise the acid catalyst, phenol, cyclohexanone, cyclohexylbenzene, and contaminants.

The acid catalyst can be at least partially soluble in the cleavage reaction mixture, is stable at a temperature of at least 185° C. and has a lower volatility (higher normal boiling point) than cyclohexylbenzene.

Acid catalysts preferably include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

The cleavage reaction preferably occurs under cleavage conditions including a temperature in a range from 20° C. to 200° C., or from 40° C. to 120° C., and a pressure in a range from 1 to 370 psig (at least 7 kPa, gauge and no greater than 2,550 kPa, gauge), or from 14.5 psig to 145 psig (from 100 kPa, gauge to 1,000 kPa, gauge) such that the cleavage reaction mixture is completely or predominantly in the liquid phase during the cleavage reaction.

The cleavage reaction mixture can contain the acid catalyst at a concentration in a range from Cac1 ppm to Cac2 ppm by weight of the total weight of the cleavage reaction mixture, where Cac1 and Cac2 can be, independently, 10, 20, 30, 40, 50, 60, 80, 100, 150, 200, 250, 300, 350, 400, 450, 500, 600, 700, 800, 900, 1000, 1500, 2000, 2500, 3000, 3500, 4000, 4500, or even 5000, as long as Cac1<Cac2. Preferably, Cac1 is 50, and Cac2 is 200.

Conversion of hydroperoxides, such as cyclohexyl-1-phenyl-1-hydroperoxide, and conveniently all cyclohexyl-1-phenyl-1-hydroperoxide and other hydroperoxides, may be very high in the cleavage reaction, e.g., at least AA wt %, where AA can be 90.0, 91.0, 92.0, 93.0, 94.0, 95.0, 96.0, 97.0, 98.0, 99.0, 99.5, 99.9, or even 100, the percentage based on the weight of a given hydroperoxide, or of all hydroperoxides fed to the cleavage step. This is desirable because any hydroperoxide, even the cyclohexyl-1-phenyl-1-hydroperoxide, becomes a contaminant in the downstream processes.

Desirably, each mole of cyclohexyl-1-phenyl-1-hydroperoxide produces one mole of phenol and one mole of cyclohexanone. However, due to side reactions, the selectivity of the cleavage reaction to phenol can range from Sph1% to Sph2% and the selectivity to cyclohexanone can range from Sch1% to Sch2%, where Sph1, Sph2, Sch1, and Sch2 can be, independently, 85, 87, 88, 89, 90, 91, 92, 93, 94, 95, 96, 97, 98, 99, or even 99.5, as long as Sph1<Sph2, and Sch1<Sch2.

Besides the cleavage feed comprising cyclohexylbenzene hydroperoxide, cyclohexylbenzene and other components originating directly from the oxidation reaction product mixture, the cleavage reaction mixture may further comprise other added materials, such as the cleavage catalyst, a solvent, and one or more products of the cleavage reaction such as phenol and cyclohexanone recycled from the cleavage product mixture, or from a downstream separation step. Thus, the cleavage reaction mixture inside the cleavage reactor may comprise, based on the total weight of the cleavage reaction mixture: (i) phenol at a concentration from CPh9 wt % to CPh10 wt %, where CPh9 and CPh10 can be, independently, 20, 25, 30, 35, 40, 45, 50, 55, 60, 65, 70, 75, or 80, as long as CPh9<CPh10; (ii) cyclohexanone at a concentration from Cch1 wt % to Cch2 wt %, where Cch1 and Cch2 can be, independently, 20, 25, 30, 35, 40, 45, 50, 55, 60, 65, 70, 75, or 80, as long as Cch1<Cch2; and (iii) cyclohexylbenzene at a concentration from Cchb7 wt % to Cchb8 wt %, where Cchb7 and Cchb8 can be, independently, 5, 8, 9, 10, 12, 14, 15, 18, 20, 22, 24, 25, 26, 28, 30, 35, 40, 45, 50, 55, 60, 65, 70, as long as Cchb7<Cchb8.

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. The cleavage reactor may comprise a plurality of reactors in series, each performing a portion of the conversion reaction, optionally operating in different modes and at different conditions selected to enhance the cleavage reaction at the pertinent conversion range. The cleavage reactor can be a catalytic distillation unit.

The cleavage reactor can be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) can be used to at least a part of the heat generated.

The cleavage product mixture exiting the cleavage reactor may comprise, based on the total weight of the cleavage product mixture: (i) phenol at a concentration from CPh11 wt % to CPh12 wt %, where CPh11 and CPh12 can be, independently, 20, 25, 30, 35, 40, 45, 50, 55, 60, 65, 70, 75, or 80, as long as Ch11<CPh12; (ii) cyclohexanone at a concentration from Cch3 wt % to Cch4 wt %, where Cch3 and Cch4 can be, independently, 20, 25, 30, 35, 40, 45, 50, 55, 60, 65, 70, 75, or 80, as long as Cch3<Cch4; and (iii) cyclohexylbenzene at a concentration from Cchb9 wt % to Cchb10 wt %, where Cchb9 and Cchb10 can be, independently, 5, 8, 9, 10, 12, 14, 15, 18, 20, 22, 24, 25, 26, 28, 30, 35, 40, 45, 50, 55, 60, 65, 70, as long as Cchb9<Cchb10.

Separation and Purification

As discussed above, the cleavage product mixture may comprise one or more contaminants. In embodiments disclosed herein, the processes further comprise contacting at least a portion of a contaminant with an acidic material to convert at least a portion of the contaminant to a converted contaminant, thereby producing a modified product mixture. Detailed description of the contaminant treatment process can be found, e.g., in International Publication WO2012/036822A1, the relevant content of which is incorporated herein by reference in its entirety.

At least a portion of the cleavage product mixture may be subjected to a neutralization reaction. Where a liquid acid such as sulfuric acid is used as the cleavage catalyst, it is highly desirable that the cleavage reaction product mixture is neutralized by a base, such as an organic amine (e.g., methylamine, ethylamine, diamines such as methylenediamine, propylene diamine, butylene diamine, pentylene diamine, hexylene diamine, and the like) before the mixture is subjected to separation to prevent equipment corrosion by the acid. Desirably, the thus formed amine sulfate salt has a boiling point higher than that of cyclohexylbenzene.

The neutralized cleavage reaction product mixture can then be separated by methods such as distillation. In one example, in a first distillation column after the cleavage reactor, a heavies fraction comprising the amine salt is obtained at the bottom of the column, a side fraction comprising cyclohexylbenzene is obtained in the middle section, and an upper fraction comprising cyclohexanone, phenol, methylcyclopentanone, and water is obtained.

The separated cyclohexylbenzene fraction can then be treated and/or purified before being delivered to the oxidizing step. Since the cyclohexylbenzene separated from the cleavage product mixture may contain phenol and/or olefins such as cyclohexenylbenzenes, the material may be subjected to treatment with an aqueous composition comprising a base as described above for the second fraction of the oxidation product mixture and/or a hydrogenation step as disclosed in, for example, WO2011/100013A1, the entire contents of which are incorporated herein by reference.

In one example, the fraction comprising phenol, cyclohexanone, and water can be further separated by simple distillation to obtain an upper fraction comprising primarily cyclohexanone and methylcyclopentanone and a lower stream comprising primarily phenol, and some cyclohexanone. Cyclohexanone cannot be completely separated form phenol without using an extractive solvent due to an azeotrope formed between these two. Thus, the upper fraction can be further distillated in a separate column to obtain a pure cyclohexanone product in the vicinity of the bottom and an impurity fraction in the vicinity of the top comprising primarily methylcyclopentanone, which can be further purified, if needed, and then used as a useful industrial material. The lower fraction can be further separated by a step of extractive distillation using an extractive solvent (e.g., glycols such as ethylene glycol, propylene glycol, diethylene glycol, triethylene glycol, and the like) described in, e.g., co-assigned, co-pending patent applications WO2013/165656A1 and WO2013/165659, the contents of which are incorporated herein by reference in their entirety. An upper fraction comprising cyclohexanone and a lower fraction comprising phenol and the extractive solvent can be obtained. In a subsequent distillation column, the lower fraction can then be separated to obtain an upper fraction comprising a phenol product and a lower fraction comprising the extractive solvent.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

The following non-limiting examples further illustrate the present invention. While the use of the catalyst prepared in the examples were only tested in benzene hydroalkylation processes, it is expected that the same catalyst would function similarly for the hydroalkylation of other aromatic compounds, such as alkylated benzenes (e.g., toluene, ethylbenzene, xylene, propylbenzene, and the like), naphthalene, and alkylated naphthalenes (e.g., methyl naphthalene, and the like).

Examples

In the Examples, Pd/MCM-49/$Al_2O_3$ catalysts having a preferential Pd distribution in the rim portion and/or outer portion of the catalyst particles (also called pellets herein) were prepared, characterized of the Pd distribution, and evaluated for performance in benzene hydroalkylation to produce cyclohexylbenzene.

1. Catalyst Preparation

Preparation of Catalyst A

A first rimmed catalyst (Catalyst A) comprising 0.15 wt % Pd on 80% MCM-49 and 20 wt % $Al_2O_3$ was prepared according to the following procedure.

a. 2.30 g of a palladium chloride solution (also containing HCl) at a Pd concentration of 19.538 wt %, commercially available from Johnson Matthey, was diluted with 327.79 g of deionized water. The pH of the combined palladium chloride and deionized water was measured to be 3.04.
  b. 300 grams of a ½0 inch (1.27 mm) quadrulobe extrudate comprising 80 wt % MCM-49, 20 wt % alumina was added to a laboratory tablet coater available from A. E. Aubin as Model #1600.
  c. The tablet coater was rotated at an rpm of 30.
  d. The palladium chloride solution prepared in step (a) was sprayed onto the rotating extrudate at 60 mL per minute.
  e. The wet extrudate continued to mix for an additional 30 minutes at a rotational speed of 10 rpm.
  f. After mixing, the wet extrudate was dried for 20 hours at 120° C. in an oven available from Desptach.
  g. The metal dispersion of the dried extrudate (0.15 wt % Pd) was measured by using a Micromeritics ASAP2100 chemisorption instrument using oxygen at a $H_2$ reduction temperature of 250° C. The measurement result was 75%.
  h. The dried extrudate was calcined in flowing air at 538° C. for three hours. The temperature was ramped from ambient to 538° C. at 1° C. per minute.
  i. The metal dispersion of the air calcined extrudate (containing 0.15 wt % Pd) was measured by using a Micromeritics ASAP2100 chemisorption instrument using oxygen at a $H_2$ reduction temperature of 250° C. The measurement result was 72%. The BET surface area was measured to be 494 m²/g. The loss-on-ignition at 525° C. was measured to be 0.7 wt %.

1.2 Preparation of Catalyst B

A second rimmed catalyst, Catalyst B, comprising 0.15 wt % Pd on 80 wt % MCM-49 and 20 wt % $Al_2O_3$, was prepared according to the following procedure.

a. 2.31 g of a palladium chloride solution (also containing HCl) at a Pd concentration of 19.480 wt %, commercially available from Johnson Matthey, was diluted with 327.97 g of deionized water. The pH of the combined palladium chloride and deionized water was measured to be 1.96.
  b. grams of a ½0 inch (1.27 mm) quadrulobe extrudate comprising 80 wt % MCM-49, 20 wt % alumina was added to a laboratory tablet coater available from A. E. Aubin as Model #1600.
  c. The tablet coater was rotated at an rpm of 30.
  d. The palladium chloride solution prepared in step (a) was sprayed onto the rotating extrudate at 60 mL per minute.
  e. The wet extrudate continued to mix for an additional 60 minutes at a rotational speed of 10 rpm.
  f. After mixing, the wet extrudate was dried for 20 hours at 120° C. in an oven available from Desptach.
  g. The metal dispersion of the dried extrudate (containing 0.15 wt % Pd) was measured by a Micromeritics ASAP2100 chemisorption instrument using oxygen after a $H_2$ reduction temperature of 250° C. The measurement result was 77%.
  h. The dried extrudate was calcined in flowing air at 538° C. for three hours. The temperature was ramped from ambient to 538° C. at 1° C. per minute.
  i. The catalyst preparation was repeated ten times in steps (a) through (h) to obtain ten batches of catalyst materials, which were then blended together.
  j. The metal dispersion of the air calcined blended 10 batches of extrudate (containing 0.15 wt % Pd) was measured by a Micromeritics ASAP2100 chemisorption instrument using oxygen at a $H_2$ reduction temperature of 250° C. The result was 73%. The BET surface area was measured to be 507 m²/g. The loss-on-ignition at 525° C. was measured to be 1.1 wt %.

2. Analysis of the Metal Distribution of the Rimmed Catalysts

A Field-Emission Electron Probe Micro Analyzer (EPMA) was utilized to generate line scans for the catalyst extrudate (also referred to as pellet) cross-sections. Catalyst extrudates were first embedded in a low viscosity epoxy resin (LR-White) under vacuum to fully impregnate them. The resin was then cured under a flow of $N_2$ at 60° C. Each cured mount was cut as shown in FIG. 2. The as-cut surface was then ground using silicon carbide grit paper (120 grit-600 grit) and then with silicon carbide powder (1000 grit) on a napped cloth to achieve a mirror finish. Samples were then coated with ~200 Å of carbon for conductivity.

EPMA conditions: 15 kV accelerating voltage, 150 nA beam current measured with an internal Faraday cup. X-ray diffracting crystals were used to detect the characteristic X-rays. A typical configuration was as follows:

| Xtal | Element X-Ray Line | Standard | Background Position (mm from peak) |
|---|---|---|---|
| LDE2: | Carbon $K\alpha_1$ | (Graphite) | +30.363, −35.653 |
| PETL: | Chlorine $K\alpha_1$ | (NaCl) | +5.000, −5.000 |
| TAPH: | Aluminum $K\alpha_1$ | ($Al_2O_3$) | +5.000, −5.000 |
| PETL: | Palladium $L\alpha_1$ | (Palladium Metal) | +5.000, −5.000 |
| TAP: | Silicon $K\alpha_1$ | ($SiO_2$) | +5.000, −5.000 |

Oxygen by difference

Peak positions for X-ray lines were determined by scanning the crystal on a standard for each set of analyses. Two background positions were checked on the sample for interferences by scanning a spectral region that encompassed both the peak and background regions. Adjustments to the peak and background positions were made as necessary to optimize the analysis (avoid overlaps, etc.).

Counting times on the catalyst pellets were typically 10 seconds on peak, and 5 seconds on each background. Net counts were calculated for each position of the beam along the line scan. Concentrations were calculated using a standard ZAF approach. A quantitative line scan is thus generated across the cross-sectioned pellet. Typically, 10-13 micron steps were used and the electron beam was defocused to match the step size. This resulted in 150 points across the pellet for a typical 1.5 mm scan (with 10 micron steps).

Before performing light optical microscopy and/or EPMA analyses, the fresh calcined hydroalkylation catalyst samples were reduced in a fixed bed reactor at 300° C. in flowing 50 psig (344 kPa gauge) $H_2$ following the same procedure as performed before hydroalkylation tests described below. After reduction, the catalyst extrudates were discharged in a $N_2$-filled glove box, then separated from the quartz diluent and loaded into sealable glass vials. The closed vials were removed from the glove box and the screw caps were slightly cracked to allow small quantities of air to slowly diffuse into the vial. This procedure provided for a controlled back-oxidation of the surface of the Pd particles in the catalyst without oxidizing the bulk of the metal. This so-called passivation procedure was performed to avoid uncontrolled oxidation and potential local overheating that might have affected metal morphology during sample handling. The thus-prepared extrudates then were epoxy-mounted, cross-sectioned and analyzed by EPMA and also imaged under a light optical microscope to characterize metal distribution.

The cross-sections of the catalyst pellets were found to have roughly symmetric geometry relative to a center line passing through the center and the two opposite corners. The line-scan of the EPMA analysis was performed along the center line.

Figure 4:
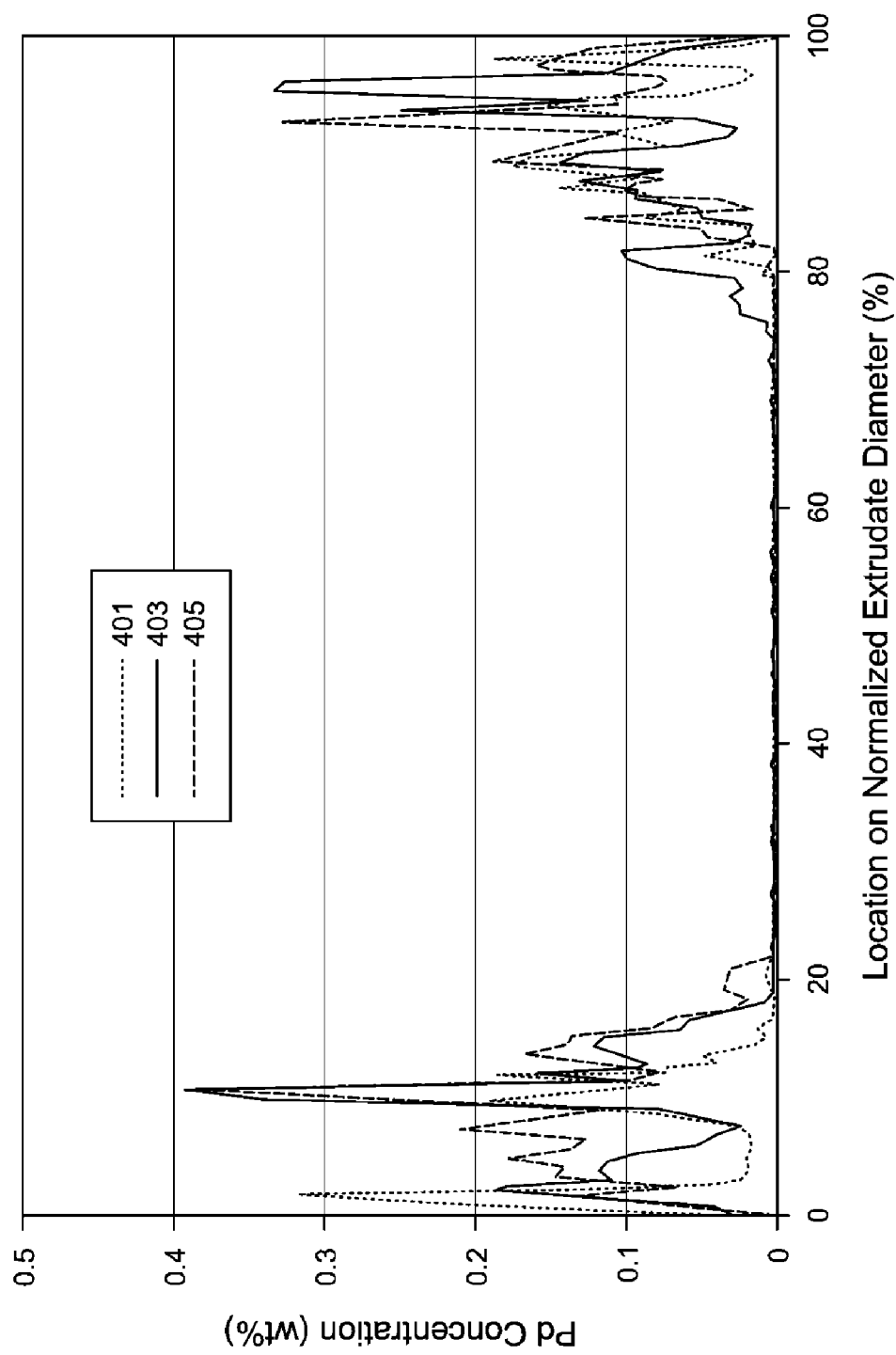
FIGS. 4 and 5 are diagrams showing Pd concentration distributions in EMPA line-scans of cross-sections of Catalyst A and Catalyst B, respectively, described in the Examples in the present disclosure.
Figure 5:
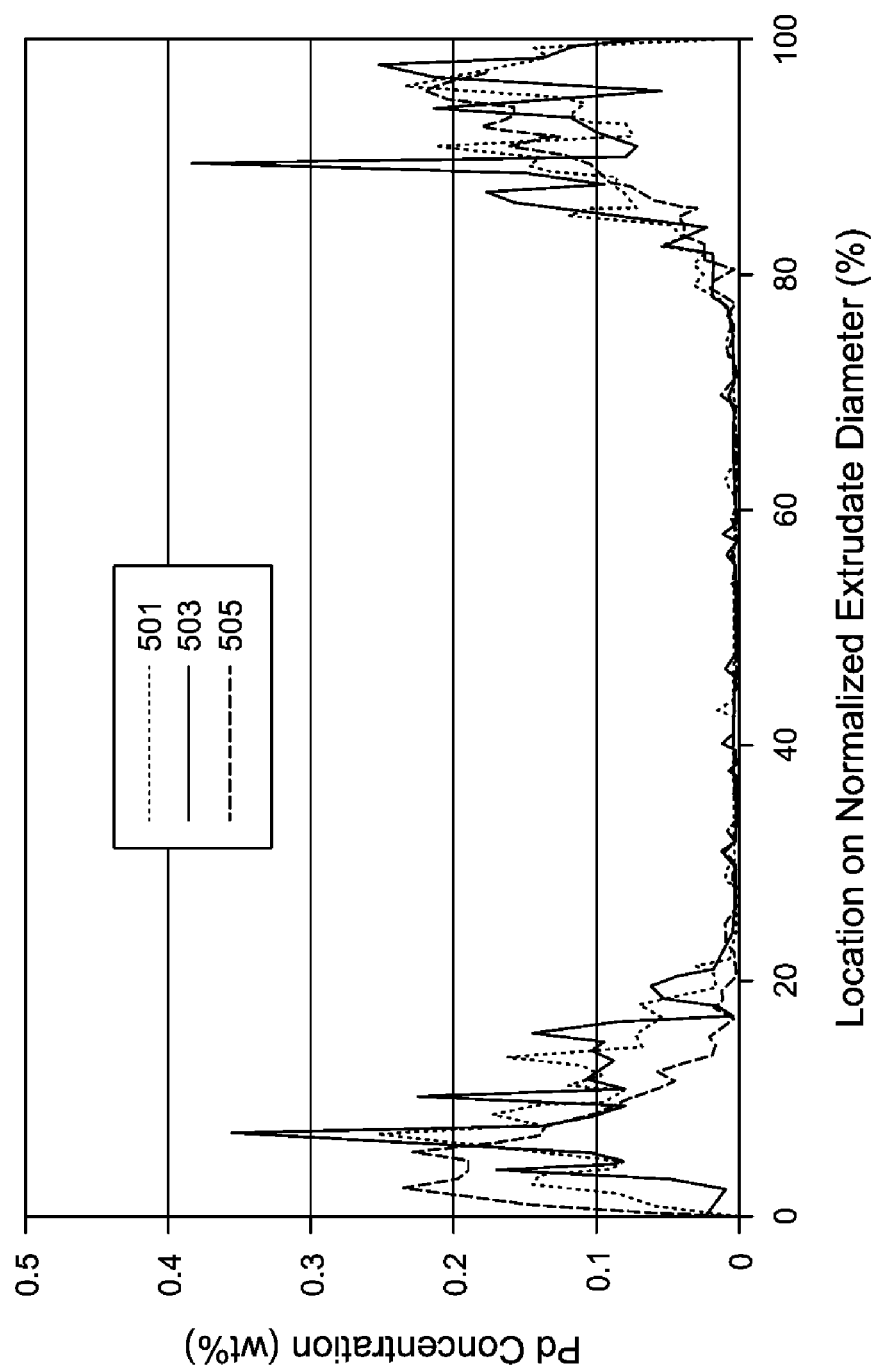

FIGS. 4 and 5 depict the EPMA line-scan results for three extrudates from Catalyst A and Catalyst B, respectively. In both figures, the horizontal axis is the location on normalized extrudate diameter (%), and the vertical axis is local Pd concentration (wt %). For each catalyst, three different pellets (401, 403, and 403 in FIG. 4 for Catalyst A, and 501, 503, and 503 in FIG. 5 for Catalyst B) were scanned. It is quite clear that in both figures, the Pd concentrations are much higher in the rim portions (left rim and right rim) than in the center portion. Indeed, both catalysts showed near-zero Pd concentration in the center portions thereof.

Tables 2.1 and 2.2 below summarize the average metal concentrations in the left rim portion (Crim(l)), right rim portion (Crim(r)), both rim portions (Crim(av)), and in the center portion (Ccenter) and their ratios for three extrudates from Catalyst A and Catalyst B, respectively. As the results show, the metal distribution within these extrudates is higher in the rim portions as evidenced by the high (~500 for Catalyst A, and ~100 or Catalyst B) Crim/Ccenter concentration ratios.

TABLE 2.1

Average metal concentration ratios for the three extrudates from Catalyst A
For 20% left and right rim portions and 20% center

| Pellet No. | Crim(l)/ Ccenter | Crim(r)/Ccenter | Crim(av)/Ccenter | Crim(l)/Crim(r) |
|---|---|---|---|---|
| 1 | 399 | 479 | 439 | 0.83 |
| 2 | 105 | 109 | 107 | 0.96 |
| 3 | 1025 | 851 | 938 | 1.20 |
| Average | 510 | 480 | 495 | 1.00 |

TABLE 2.2

Average metal concentration ratios for the three extrudates from Catalyst B
For 20% left and right rim portions and 20% center

| Pellet No. | Crim(l)/ Ccenter | Crim(r)/Ccenter | Crim(av)/Ccenter | Crim(l)/Crim(r) |
|---|---|---|---|---|
| 1 | 162 | 167 | 164 | 0.97 |
| 2 | 48 | 58 | 53 | 0.83 |
| 3 | 112 | 133 | 122 | 0.84 |
| Average | 107 | 119 | 113 | 0.88 |

Tables 2.3 and 2.4 below summarize the average metal concentrations in the left outer portion (Couter(l)), right outer portion (Couter(r)), both outer portions (Couter(av)), and in the center portion (Ccenter) and their ratios for three extrudates from Catalyst A and Catalyst B, respectively. As the results show, the metal distribution within these extrudates is higher in the outer portions as evidenced by the high (377-401 for Catalyst A and 74-80 for Catalyst B) Couter/Ccenter concentration ratios.

TABLE 2.3

Average metal concentration ratios for the three extrudates from Catalyst A
For 30% left and right outer portions and 20% center

| Pellet No. | Couter(l)/ Ccenter | Couter(r)/Ccenter | Couter(av)/Ccenter | Couter(l)/ Couter(r) |
|---|---|---|---|---|
| 1 | 362 | 539 | 451 | 0.67 |
| 2 | 72 | 80 | 76 | 0.91 |
| 3 | 697 | 584 | 641 | 1.19 |
| Average | 377 | 401 | 389 | 0.92 |

TABLE 2.4

Average metal concentration ratios for the three extrudates from Catalyst B
For 30% left and right outer portions and 30% center

| Pellet No. | Couter(l)/ Ccenter | Couter(r)/Ccenter | Couter(av)/Ccenter | Couter(l)/ Couter(r) |
|---|---|---|---|---|
| 1 | 110 | 111 | 111 | 0.99 |
| 2 | 34 | 40 | 37 | 0.86 |
| 3 | 77 | 90 | 84 | 0.85 |
| Average | 74 | 80 | 77 | 0.90 |

3. Hydroalkylation Tests with Rimmed Catalysts

Hydroalkylation tests were performed in a down-flow 0.5" (12.7 mm) diameter stainless steel fixed bed reactor that was equipped with a three-point thermocouple positioned at the center of the reactor tube. The 4.5" (114 mm) long catalyst bed was positioned to ensure that three thermocouples (placed 2 inches (5 cm) apart) measured the temperatures at the inlet, outlet and the center of the catalyst bed. In order to reduce the volumetric heat release and thus to afford more isothermal operations, the catalyst was diluted with quartz. The diluent also enhanced the even distribution of the reactants in the catalyst bed. Neat quartz was used at either side of the catalyst bed. The quartz served to preheat and evenly distribute the feed at the feed inlet side and to hold the catalyst bed at the exit side, the latter of which was at the bottom of the reactor (downflow).

The reactor was encased in a 6 inch (15 cm) long and 1 inch (2.5 cm) diameter brass sleeve that was centered along the catalyst bed to improve its temperature control. Housed in the brass sleeve were the three thermocouples positioned at the two ends and the center of the catalyst bed. The reactor was heated by a three-zone clam-shell electrical furnace. During steady-state operations, the temperatures of the three furnace zones were controlled by utilizing the feedback from the three thermocouples in the brass sleeve of the reactor. The catalyst bed temperatures at the three thermocouples were typically within 2° C. of the set value. The reported reaction temperatures ($T_{rxn}$) were calculated as the weighted average of the three thermocouple measurements ($T_{inlet}$, $T_{middle}$, $T_{outlet}$) by the following formula:

$$T_{rxn} = (T_{inlet} + 2T_{middle} + T_{outlet})/4.$$

The catalysts in all experiments nominally contained 0.15 wt % Pd supported on alumina-bound MCM-49 (alumina/MCM-49 of 20/80 wt/wt). The catalyst was received in its calcined form as 1/20" (1.27 mm) extrudate and was stored in closed plastic bottles. Before charging to the reactor, the catalyst extrudates were broken up along their length and sized to a length/diameter (L/D) ratio of near one (14-20 mesh) to afford the reactor beds with proper hydrodynamics. As mentioned above, the catalyst was also diluted with quartz that on one hand reduced volumetric catalyst charge and thus volumetric heat release while also improving the desired plug-flow characteristic of the reactant stream passing through the catalyst bed.

In a typical hydroalkylation test, nominally 2 g of 14-20 mesh catalyst diluted with nominally 6 g quartz was charged into the reactor. The moisture content of the as-loaded catalyst was nominally 12 wt %, thus the dry catalyst load was typically 1.76 g. After pressure testing, the catalyst was activated at 50 psig (345 kPa gauge) in flowing pure hydrogen. The hydrogen treatment was finished by letting the catalyst cool down to near the hydroalkylation temperature (145° C.) while keeping the pressure and hydrogen flow rate unchanged. The catalyst then was brought on hydroalkylation stream by first increasing the pressure to 165 psig (1138 kPa gauge), then reducing the hydrogen flow rate to 18 sccm (standard cubic centimeter) and introducing benzene at 1 mL/min flow rate. This condition was maintained for 1 hour to ensure that the catalyst bed was properly wetted after which the benzene flow rate was reduced to 0.096 mL/min corresponding to a nominal 0.7 mol $H_2$/mol benzene feed composition and 2.5 weight benzene/weight catalyst/h (or 2.5/h) weight hourly space velocity (WHSV) on an as-loaded basis (i.e., catalyst with a nominal moisture content of 12 wt %).

After letting the reactor line out for about 6 hours, the product effluent was periodically directed to a chilled knock-out vessel held at about 5° C. and liquid samples were collected then analyzed by a gas chromatograph equipped with a flame-ionization detector (FID). The response factors for the various product components were determined either using blends of authentic samples or by using factors published in the Journal of Gas Chromatography in February 1967, p 68 by W. A. Dietz. Calibrations were checked by analyzing gravimetrically prepared calibration blends. Benzene conversion and product selectivity were determined from the normalized FID areas by applying the calibration response factors.

Two different rimmed catalyst batches were tested in benzene hydroalkylation. The conditions, benzene conversion, and selectivity results are listed in Table 3.1.

TABLE 3.1

Benzene conversion and hydroalkylation selectivity with rimmed catalysts

| Run No. | Catalyst | Benzene Conversion (%) | Selectivity (wt %) | | | | |
|---|---|---|---|---|---|---|---|
| | | | cHex | CHB | C18 | CHB + C18 | cHex + CHB + C18 |
| A1 | A | 35 | 9 | 79 | 10 | 89 | 98 |
| A2 | A | 37 | 10 | 79 | 10 | 89 | 99 |
| B3 | B | 36 | 9 | 77 | 13 | 90 | 99 |

0.15 wt % Pd/MCM-49-$Al_2O_3$ catalyst at 145° C., 165 psig (1138 kPa gauge), $H_2$/benzene molar ratio of 0.7, and 2.5/h benzene WHSV
Activation conditions: 50 psig hydrogen at a flow rate of 82-84 standard cubic cm/min/g catalyst (1980-2028/h GHSV), ramp nominally from ambient temperature to 300° C. at 60° C./hour, hold at 300° C. for 2 hours
cHex = cyclohexane, CHB = cyclohexylbenzene, C18 = 18-carbon fraction benzene
WHSV = benzene weight hourly space velocity = g benzene/g catalyst/h Both catalysts demonstrated surprisingly high alkylation selectivities as demonstrated by the combined 86% cyclohexylbenzene and dicyclohexylbenzene selectivity. Catalytic activity was also excellent as shown by the 35-36% benzene conversion. Note that benzene conversion was limited to less than 100% by the sub-stoichiometric hydrogen feed set for reducing the yield or the cyclohexane by-product.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

Non-limiting embodiments of the present disclosure include:

E1. A process for producing an alkylated aromatic compound, the process comprising contacting an aromatic starting material and hydrogen with a plurality of catalyst particles under hydroalkylation conditions to produce an effluent comprising the alkylated aromatic compound, the catalyst comprising a composite of a solid acid, an inorganic oxide different from the molecular sieve and a hydrogenation metal, wherein the distribution of the hydrogenation metal in at least 60 wt % of the catalyst particles is such that:

the average concentration of the hydrogenation metal in the rim portion of a given catalyst particle is Crim;

the average concentration of the hydrogenation metal in the outer portion of a given catalyst particle is Couter; and the average concentration of the hydrogenation metal in the center portion of the given catalyst particle is Ccenter; and at least one of the following conditions is met:
(i) Crim/Ccenter≥2.0; and
(ii) Couter/Ccenter≥2.0.

E2. The process of E1, wherein the solid acid comprises a molecular sieve.

E3. The process of E1 or E2, wherein in at least 80 wt % of the catalyst particles, at least one of the following conditions is met:
(i) Crim/Ccenter≥2.0; and
(ii) Couter/Ccenter≥2.0.

E4. The process of any of E1 to E3, wherein at least one of the following conditions is met: (i) Crim/Ccenter≥10.0; and (ii) Couter/Ccenter≥10.0.

E5. The process of any of E1 to E4, wherein at least 50 wt % of the hydrogenation metal is supported on the inorganic oxide.

E6. The process of E4, wherein at least 75 wt % of the hydrogenation metal is supported on the inorganic oxide.

E7. The process of any of E1 to E6, wherein the molecular sieve is a MWW type molecular sieve.

E8. The process of E7, wherein the molecular sieve comprises at least one of MCM-22, PSH-3, SSZ-25, ERB-1, ITQ-1, ITQ-2, MCM-36, MCM-49, and MCM-56.

E9. The process of any of E1 to E8, wherein the inorganic oxide comprises an oxide of at least one element of Groups 2, 4, 13, and 14 of the Periodic Table of Elements.

E10. The process of E9, wherein the inorganic oxide comprises at least one of alumina, silica, titania, and zirconia.

E11. The process of any of E1 to E10, wherein the hydrogenation metal comprises at least one of Pd, Pt, Ru, Ni, Zr, Ru, Ir, Rh, Os and Co.

E12. The process of E11, wherein the hydrogenation metal is Pd, and at least 60 wt % of Pd is supported on the inorganic oxide support.

E13. The process of any of E1 to E12, wherein the catalyst particles are made by a catalyst fabrication process comprising:
(I) forming a mixture comprising the molecular sieve and the inorganic oxide;
(II) forming a pellet from the mixture;
(III) depositing a source material of the hydrogenation metal onto the pellet; and
(IV) calcining the pellet after step (III) at a temperature in the range from 400° C. to 1000° C.

E14. The process of E13, wherein the catalyst fabrication process further comprises, after step (IV):
(V) activating the calcined pellet in the presence of an atmosphere comprising $H_2$.

E15. The process of E13 or E14, wherein in step (III), the source material of the hydrogenation metal comprises $PdCl_2$, and step (III) comprises impregnating the pellet with an aqueous $PdCl_2$ dispersion having a pH in the range from 0 to 4.

E16. The process of any of E1 to E12, wherein the catalyst particles are made by a catalyst fabrication process comprising:
(i) depositing a source material of the hydrogenation metal onto a plurality of particles of the inorganic oxide;
(ii) mixing the particles of the inorganic oxide resulting from step (i) with a plurality of particles of the molecular sieve;
(iii) forming a pellet from the mixture resulting from step (ii);
(iv) calcining the pellet at a temperature in the range from 400° C. to 1000° C.

E17. The process of E16, wherein in step (i), the source material of the hydrogenation metal comprises $PdCl_2$, and step (i) comprises impregnating the particles of the inorganic oxide with an aqueous $PdCl_2$ dispersion having a pH in the range from 0 to 4.

E18. The process of E16 or E17, wherein the catalyst fabrication process further comprises, after step (iv):
(v) activating the calcined pellet in the presence of an atmosphere comprising $H_2$.

E19. The process of any of E1 to E12, wherein the catalyst particles are made by a catalyst fabrication process comprising:
(a) depositing a source material of the hydrogenation metal onto a plurality of particles of the inorganic oxide;
(b) calcining the particles of the inorganic oxide resulting from step (a) at a temperature in the range form 400° C. to 1000° C.;
(c) mixing the particles of the inorganic oxide resulting from step (b) with a plurality of particles of the molecular sieve;
(d) forming a pellet from the mixture resulting from step (c); and
(e) calcining the pellet at a temperature in the range from 400° C. to 1000° C.

E20. The process of E19, wherein the catalyst fabrication process further comprises, after step (e):
(f) activating the calcined pellet in the presence of an atmosphere comprising $H_2$.

E21. The process of any of E1 to E20, wherein the aromatic starting material comprises benzene and/or an alkyl benzene.

E22. The process of E21, wherein the aromatic starting material is benzene and the alkylated aromatic compound is cyclohexylbenzene.

E23. The process of E22, wherein the molar ratio of hydrogen to benzene in the contacting step is in the range from 0.15:1 to 15:1.

E24. The process of E23, wherein the molar ratio of hydrogen to benzene in the contacting step is in the range from 0.3:1 to 1.0:1.

E25. The process of any of E1 to E24, wherein in the contacting step, a cyclic aliphatic compound is produced, and the process further comprises:
dehydrogenating at least a portion of the cyclic aliphatic compound to produce a dehydrogenation stream comprising the aromatic starting material; and
recycling at least part of the dehydrogenation stream to the contacting step.

E26. The process of E25, wherein:
the aromatic starting material comprises benzene; and the cyclic aliphatic compound is cyclohexane.

E27. A process for making phenol and/or cyclohexanone, the process comprising:
(1) producing cyclohexylbenzene according to any of E22 to E26;
(2) oxidizing at least a portion of the cyclohexylbenzene to produce cyclohexylbenzene hydroperoxide; and
(3) cleaving at least a portion of the cyclohexylbenzene hydroperoxide to obtain phenol and cyclohexanone.

E28. A catalyst, the catalyst comprising a composite of a molecular sieve, an inorganic oxide different from the molecular sieve and a hydrogenation metal, wherein the distribution of the hydrogenation metal in at least 60 wt % of the catalyst particles is such that:

the average concentration of the hydrogenation metal in the rim portion of a given catalyst particle is Crim;
the average concentration of the hydrogenation metal in the outer portion of a given catalyst particle is Couter; and
the average concentration of the hydrogenation metal in the center portion of the given catalyst particle is Ccenter; and
at least one of the following conditions is met:
(i) Crim/Ccenter≥2.0; and
(ii) Couter/Ccenter≥2.0.

E29. The catalyst of E28, wherein at least one of the following conditions is met: (i) Crim/Ccenter≥10.0; and (ii) Couter/Ccenter≥10.0.

E30. The catalyst of E28 or E29, wherein the solid acid comprises a molecular sieve.

E31. The catalyst of any of E28 to E30, wherein at least 50 wt % of the hydrogenation metal is supported on the inorganic oxide.

E32. The catalyst of any of E28 to E31, wherein at least 75 wt % of the hydrogenation metal is supported on the inorganic oxide.

E33. The catalyst of any of E28 to E32, wherein the inorganic oxide is present in the composite in the form of islets, and the islets are substantially uniformly distributed within the composite.

E34. The catalyst of E33, wherein the inorganic oxide islets have an average size of at most 40 μm.

E35. The catalyst of any of E28 to E34, wherein the molecular sieve is a MWW type molecular sieve.

E36. The catalyst of E35, wherein the molecular sieve comprises at least one of MCM-22, PSH-3, SSZ-25, ERB-1, ITQ-1, ITQ-2, MCM-36, MCM-49, and MCM-56.

E37. The catalyst of any of E28 to E36, wherein the inorganic oxide comprises an oxide of at least one element of Groups 2, 4, 13, and 14 of the Periodic Table of Elements.

E38. The catalyst of any of E28 to E37, wherein the inorganic oxide comprises at least one of alumina, silica, titania, and zirconia.

E39. The catalyst of any of E28 to E38, wherein the hydrogenation metal comprises at least one of Pd, Pt, Ru, Ni, Zr, Ru, Ir, Rh, Os and Co.

E40. The catalyst of E39, wherein at least 99 wt % of the hydrogenation metal has an oxidation state of zero.

The invention claimed is:

1. A process for producing an alkylated aromatic compound, the process comprising contacting an aromatic starting material and hydrogen with a plurality of catalyst particles under hydroalkylation conditions to produce an effluent comprising the alkylated aromatic compound, the catalyst comprising a composite of a solid acid, an inorganic oxide different from the solid acid and a hydrogenation metal, wherein the distribution of the hydrogenation metal in at least 60 wt % of the catalyst particles is such that:
the average concentration of the hydrogenation metal in the rim portion of a given catalyst particle is Crim;
the average concentration of the hydrogenation metal in the outer portion of a given catalyst particle is Couter; and
the average concentration of the hydrogenation metal in the center portion of the given catalyst particle is Ccenter; and
at least one of the following conditions is met:

$$\text{Crim/Ccenter} \geq 2.0; \text{ and} \qquad (i)$$

$$\text{Couter/Ccenter} \geq 2.0. \qquad (ii)$$

2. The process of claim 1, wherein the solid acid comprises a molecular sieve.

3. The process of claim 1, wherein in at least 80 wt % of the catalyst particles, at least one of the following conditions is met: (i) Crim/Ccenter≥2.0; and (ii) Couter/Ccenter≥2.0.

4. The process of claim 1, wherein at least one of the following conditions is met: (a) Crim/Ccenter≥10.0; and (b) Couter/Ccenter≥10.0.

5. The process of claim 1, wherein at least 50 wt % of the hydrogenation metal is supported on the inorganic oxide.

6. The process of claim 1, wherein the solid acid is a MWW type molecular sieve.

7. The process of claim 6, wherein the solid acid comprises at least one of the following molecular sieves: MCM-22, PSH-3, SSZ-25, ERB-1, ITQ-1, ITQ-2, MCM-36, MCM-49, and MCM-56.

8. The process of claim 1, wherein the inorganic oxide comprises at least one of alumina, silica, titania, and zirconia.

9. The process of claim 1, wherein the hydrogenation metal comprises at least one of Pd, Pt, Ru, Ni, Zr, Ru, Ir, Rh, Os and Co.

10. The process of claim 1, wherein the catalyst particles are made by a catalyst fabrication process comprising:
(I) forming a mixture comprising the solid acid and the inorganic oxide;
(II) forming a pellet from the mixture;
(III) depositing a source material of the hydrogenation metal onto the pellet; and
(IV) calcining the pellet after step (III) at a temperature in the range from 400° C. to 1000° C.

11. The process of claim 10, wherein the source material of the hydrogenation metal comprises $PdCl_2$, and the depositing step comprises impregnating the pellet with an aqueous $PdCl_2$ dispersion having a pH in the range from 0 to 4.

12. The process of claim 10, wherein the catalyst fabrication process further comprises, after step (IV):
(V) activating the calcined pellet in the presence of $H_2$.

13. The process of claim 1, wherein the aromatic starting material is benzene and the alkylated aromatic compound is cyclohexylbenzene.

14. A process for making phenol and/or cyclohexanone, the process comprising:
(1) producing cyclohexylbenzene according to claim 13;
(2) oxidizing at least a portion of the cyclohexylbenzene to produce cyclohexylbenzene hydroperoxide; and
(3) cleaving at least a portion of the cyclohexylbenzene hydroperoxide to obtain phenol and cyclohexanone.

15. A catalyst, the catalyst comprising a composite of a solid acid, an inorganic oxide different from the solid acid and a hydrogenation metal, wherein the distribution of the hydrogenation metal in at least 60 wt % of the catalyst particles is such that:
the average concentration of the hydrogenation metal in the rim portion of a given catalyst particle is Crim;
the average concentration of the hydrogenation metal in the outer portion of a given catalyst particle is Couter; and
the average concentration of the hydrogenation metal in the center portion of the given catalyst particle is Ccenter; and at least one of the following conditions is met:

$C_{rim}/C_{center} \geq 2.0$; and (i)

$C_{outer}/C_{center} \geq 2.0$. (ii)

16. The catalyst of claim 15, wherein at least one of the following conditions is met: (a) $C_{rim}/C_{center} \geq 10.0$; and (b) $C_{outer}/C_{center} \geq 10.0$.

17. The catalyst of claim 15, wherein at least 50 wt % of the hydrogenation metal is supported on the inorganic oxide.

18. The catalyst of claim 15, wherein at least 75 wt % of the hydrogenation metal is supported on the inorganic oxide.

19. The catalyst of claim 15, wherein the inorganic oxide is present in the composite in the form of islets, and the islets are substantially uniformly distributed within the composite.

20. The catalyst of claim 19, wherein the inorganic oxide islets have an average size of at most 40 μm.

21. The catalyst of claim 15, wherein the solid acid is a MWW type molecular sieve.

22. The catalyst of claim 21, wherein the solid acid comprises at least one of the following molecular sieves: MCM-22, PSH-3, SSZ-25, ERB-1, ITQ-1, ITQ-2, MCM-36, MCM-49, and MCM-56.

23. The catalyst of claim 15, wherein the inorganic oxide comprises at least one of alumina, silica, titania, and zirconia.

24. The catalyst of claim 15, wherein the hydrogenation metal comprises at least one of Pd, Pt, Ru, Ni, Zr, Ru, Ir, Rh, Os and Co.

25. The catalyst of claim 24, wherein at least 90 wt % of the hydrogenation metal has an oxidation state of zero.

\* \* \* \* \*